US009655865B2

(12) United States Patent
Cincotta

(10) Patent No.: US 9,655,865 B2
(45) Date of Patent: May 23, 2017

(54) THERAPEUTIC TREATMENT FOR METABOLIC SYNDROME, TYPE 2 DIABETES, OBESITY, OR PREDIABETES

(75) Inventor: Anthony H. Cincotta, Tiverton, RI (US)

(73) Assignee: VeroScience, LLC, Tiverton, RI (US)

( * ) Notice: Subject to any disclaimer, the term of this patent is extended or adjusted under 35 U.S.C. 154(b) by 774 days.

(21) Appl. No.: 12/154,907

(22) Filed: May 28, 2008

(65) Prior Publication Data

US 2008/0293735 A1 Nov. 27, 2008

Related U.S. Application Data

(63) Continuation-in-part of application No. 10/944,660, filed on Sep. 17, 2004, now abandoned, which is a continuation-in-part of application No. 10/627,014, filed on Jul. 25, 2003, now abandoned.

(60) Provisional application No. 60/399,180, filed on Jul. 29, 2002, provisional application No. 60/932,071, filed on May 29, 2007.

(51) Int. Cl.
| | | |
|---|---|---|
| A01N 43/42 | (2006.01) | |
| A61K 31/44 | (2006.01) | |
| A61K 31/00 | (2006.01) | |
| A61K 31/48 | (2006.01) | |
| A61K 45/06 | (2006.01) | |

(52) U.S. Cl.
CPC .............. A61K 31/00 (2013.01); A61K 31/48 (2013.01); A61K 45/06 (2013.01)

(58) Field of Classification Search
None
See application file for complete search history.

(56) References Cited

U.S. PATENT DOCUMENTS

| | | | |
|---|---|---|---|
| 4,659,715 A | 4/1987 | Meier et al. | |
| 4,783,469 A | 11/1988 | Meier et al. | |
| 4,791,125 A | 12/1988 | Clark | |
| 5,006,526 A | 4/1991 | Meier et al. | |
| 5,344,832 A | 9/1994 | Cincotta et al. | |
| 5,468,755 A | 11/1995 | Cincotta et al. | |
| 5,496,803 A | 3/1996 | Meier et al. | |
| 5,554,623 A | 9/1996 | Cincotta et al. | |
| 5,565,454 A | 10/1996 | Cincotta | |
| 5,585,347 A | 12/1996 | Meier et al. | |
| 5,626,860 A | 5/1997 | Cincotta et al. | |
| 5,635,512 A | 6/1997 | Cincotta et al. | |
| 5,654,313 A | 8/1997 | Cincotta et al. | |
| 5,668,155 A | 9/1997 | Cincotta et al. | |
| 5,679,685 A | 10/1997 | Cincotta et al. | |
| 5,688,794 A | 11/1997 | Meier et al. | |
| 5,696,128 A | 12/1997 | Cincotta et al. | |
| 5,700,795 A | 12/1997 | Cincotta et al. | |
| 5,700,800 A | 12/1997 | Cincotta et al. | |
| 5,712,265 A | 1/1998 | Cincotta et al. | |
| 5,714,519 A | 2/1998 | Cincotta et al. | |
| 5,716,932 A | 2/1998 | Meier et al. | |
| 5,716,933 A | 2/1998 | Meier et al. | |
| 5,716,957 A | 2/1998 | Cincotta et al. | |
| 5,716,962 A | 2/1998 | Cincotta et al. | |
| 5,719,160 A | 2/1998 | Cincotta et al. | |
| 5,731,287 A | 3/1998 | Meier et al. | |
| 5,731,312 A | 3/1998 | Cincotta et al. | |
| 5,741,503 A * | 4/1998 | Cincotta et al. .............. 424/423 |
| 5,744,477 A | 4/1998 | Cincotta et al. | |
| 5,750,519 A | 5/1998 | Cincotta et al. | |
| 5,756,513 A | 5/1998 | Cincotta et al. | |

(Continued)

FOREIGN PATENT DOCUMENTS

| | | |
|---|---|---|
| CN | 1678313 | 10/2005 |
| JP | 9301892 | 11/1997 |
| RU | 2467743 | 11/2012 |
| WO | WO 93/12793 A1 | 7/1993 |
| WO | WO 97/41873 A1 | 11/1997 |
| WO | WO02/054652 | 7/2002 |
| WO | 2004010946 | 2/2004 |
| WO | WO2004/010946 A2 | 2/2004 |

OTHER PUBLICATIONS

Gadde et al "Bupropion for weight loss: An investigation of efficacy and tolerability in overweight and obese women", Obesity Research, vol. 9, No. 9, Sep. 2001, pp. 544-551.*

(Continued)

*Primary Examiner* — Jean Cornet
(74) *Attorney, Agent, or Firm* — Fish & Richardson P.C.

(57) ABSTRACT

The present invention is directed to a method for treating a patient suffering from the metabolic syndrome, Type 2 diabetes, obesity, or prediabetes, comprising the step of increasing the ratio of dopaminergic neuronal to noradrenergic neuronal activity within the central nervous system and particularly the hypothalamus of the central nervous system of the patient.

In another aspect, the present invention is directed to a method for treating a patient suffering from a metabolic disorder such as the metabolic syndrome, Type 2 diabetes, obesity, or prediabetes, and the metabolic sequale of these diseases including cardiovascular, cerebrovascular, renal and hepatic diseases, comprising the step of: administering to a patient suffering from the metabolic syndrome, Type 2 diabetes, obesity, or prediabetes a pharmaceutical composition comprising (1) at least one compound that stimulates an increase in central dopaminergic neuronal activity level in the subject, and (2) at least one compound that stimulates a decrease in central noradrenergic neuronal activity level in the subject. The present invention is also directed to pharmaceutical compositions that include the above compounds and a pharmaceutically acceptable carrier.

5 Claims, 12 Drawing Sheets

(56) References Cited

U.S. PATENT DOCUMENTS

| | | | |
|---|---|---|---|
| 5,760,047 | A | 6/1998 | Cincotta et al. |
| 5,792,748 | A | 8/1998 | Cincotta et al. |
| 5,830,895 | A | 11/1998 | Cincotta et al. |
| 5,854,255 | A | 12/1998 | Cincotta et al. |
| 5,866,584 | A | 2/1999 | Cincotta et al. |
| 5,872,127 | A | 2/1999 | Cincotta et al. |
| 5,872,133 | A | 2/1999 | Cincotta et al. |
| 5,877,183 | A | 3/1999 | Cincotta |
| 5,902,811 | A | 5/1999 | Cincotta |
| 5,905,083 | A | 5/1999 | Cincotta et al. |
| 6,004,972 | A | 12/1999 | Cincotta et al. |
| 6,071,914 | A | 6/2000 | Cincotta et al. |
| 6,075,020 | A | 6/2000 | Cincotta et al. |
| 6,855,707 | B2 | 2/2005 | Cincotta |
| 7,888,310 | B2 | 2/2011 | Cincotta |
| 8,021,681 | B2 | 9/2011 | Cincotta |
| 8,137,992 | B2 | 3/2012 | Cincotta |
| 8,137,993 | B2 | 3/2012 | Cincotta |
| 8,137,994 | B2 | 3/2012 | Cincotta |
| 8,431,155 | B1 | 4/2013 | Cincotta et al. |
| 8,613,947 | B2 | 12/2013 | Cincotta et al. |
| 8,741,918 | B2 | 6/2014 | Cincotta |
| 8,821,915 | B2 | 9/2014 | Cincotta |
| 8,877,708 | B2 | 11/2014 | Cincotta |
| 9,192,576 | B2 | 11/2015 | Cincotta et al. |
| 9,205,084 | B2 | 12/2015 | Cincotta |
| 9,352,025 | B2 | 5/2016 | Cincotta |
| 2001/0016582 | A1 | 8/2001 | Cincotta et al. |
| 2002/0187985 | A1 | 12/2002 | Cincotta |
| 2004/0077679 | A1 | 4/2004 | Cincotta |
| 2004/0081678 | A1 | 4/2004 | Cincotta |
| 2004/0214887 | A1 | 10/2004 | Dasseux et al. |
| 2004/0220190 | A1 | 11/2004 | Cincotta |
| 2005/0054652 | A1 | 3/2005 | Cincotta |
| 2005/0054734 | A1 | 3/2005 | Cincotta |
| 2005/0215558 | A1 | 9/2005 | Cincotta |
| 2008/0200453 | A1 | 8/2008 | Cincotta |
| 2009/0137598 | A1 | 5/2009 | Cincotta |
| 2009/0143390 | A1 | 6/2009 | Cincotta |
| 2010/0035886 | A1 | 2/2010 | Cincotta et al. |
| 2013/0197005 | A1 | 8/2013 | Cincotta |
| 2013/0274246 | A1 | 10/2013 | Cincotta |
| 2014/0051685 | A1 | 2/2014 | Cincotta |
| 2014/0249136 | A1 | 9/2014 | Cincotta |
| 2014/0342975 | A1 | 11/2014 | Cincotta |
| 2015/0011554 | A1 | 1/2015 | Cincotta et al. |
| 2015/0024995 | A1 | 1/2015 | Cincotta |
| 2015/0335641 | A1 | 11/2015 | Cincotta |
| 2016/0038424 | A1 | 2/2016 | Cincotta et al. |

OTHER PUBLICATIONS

Grundy, Scott M., "Drug therapy of the metabolic syndrome: minimizing the emerging crisis in polypharmacy", Nature Reviews/Drug Discovery, vol. 5, pp. 295-309 (Apr. 2006).

Piacentini, M. F. et al., "Effect of bupropion on hippocampal neurotransmitters and on peripheral hormonal concentrations in the rat", Journal of Applied Physiology, vol. 95, [Ref. 4. Continued] pp. 652-656 (2003).

Wimalasena, Kandatege et al., "Chiral Multisubstrate Inhibitors of Dopamine-Monooxygenase: Evidence for Dual Modes of Interaction", American Chemical Society/Biochemistry, [Ref. 5. Continued] vol. 36, pp. 7144-7153 (1997).

Kok, Petra et al., "*Activation of dopamine D2 receptors simultaneously ameliorates various metabolic features of obese women*", American Journal of Physiology—Endocrinology and Metabolism, vol. 291, pp. E1038-E1043 (Jun. 27, 2006).

Mannelli, Massimo et al., "*Effects of Different Dopaminergic Antagonists on Bromocriptine-Induced Inhibition of Norepinephrine Release*", Journal of Clinical Endocrinology and Metabolism, vol. 59, No. 1, pp. 74-78 (1984).

Caveno, Icilio et al., "*Heart Rate Lowering Effects of N, N-di-n-Propyl-Dopamine in Rats: Evidence for Stimulation of Central Dopamine Receptors Leading to Inhibition of Sympathetic Tone and Enhancement of Parasympathetic Outflow*", Journal of Pharmacology and Experimental Therapeutics, vol. 219, No. 2, pp. 510-519 (1981).

The Lipid, vol. 16, No. 3, pp. 265-270 (2005); No English Abstract.

Sajki, Atsuhito et al., "The role of anti-obesic in the treatment of metabolic syndrome", Journal of Clinical Experimental Medicine, vol. 213, No. 5, pp. 643-649 (2005); No English Abstract.

Zhang, Ying et al., "Bromocriptine/SKF38393 Treatment Ameliorates Dyslipidemia in ob/ob Mice", Metabolism, vol. 48, No. 8, pp. 1033-1040 (1999). In English.

sraeli Official Action dated Feb. 19, 2014 which issued in corresponding Israel Patent Application No. 202269.

Canadian Office Action which issued on Jan. 7, 2014 in corresponding Canadian Application No. 2,688,035.

Armentero et al., "Dopamine Receptor Agonists Media neuroprotection in malonate-Induced striatal lesion in the Rat," Experimental Neurology, Dec. 2002, 178(2):301-305.

Arteriosclerosis/atherosclerosis Definition-Diseases and Condition, By Mayo Clinic staff, May 2014 accessed on Oct. 8, 2014; available at http://www.mayoclinic.org/diseases-conditions/arteriosclerosis/basics/definition/con-20026972, 9 pages.

Breen et al., "Insulin increases reendothelialization and inhibits cell migration and neointimal growth after arterial injury," Arterioscler Thromb Vase Biol. 2009, 29:1060-1066.

Bruemmer et al., "Thiazolidinedione regulation of smooth muscle cell proliferation," The American Journal of Medicine, Dec. 8, 2003, 115(BA):87S-92S.

Communication Pursuant to Article 94(3) EPC issued in EP Application No. 08768002.1, dated Jan. 15, 2014, 7 pages.

Communication Pursuant to Article 94(3) EPC issued in EP Application No. 08768002.1, dated Apr. 20, 2011, 4 pages.

Communication Pursuant to Article 94(3) EPC issued in EP Application No. 08742225.9, dated Dec. 23, 2014, 4 pages.

Dai et al., "LOX-1, a bridge between GLP-1 and mitochondrial ROS generation in human vascular smooth muscle cells," Biochemical and Biophysical Research Communications, 2013, 437:62-66.

Dios et al., "Troglitazone, but not rosiglitazone, inhibits na/h exchange activity and proliferation of macrovascular endothelial cells," Journal of Diabetes and its Complications, 2001, 15:120-127.

Dormandy et al., "Secondary prevention of macrovascular events in patients with type 2 diabetes in the PROactive Study (PROspective pioglitazone Clinical Trial in macrovascular events): a randomised controlled trial," Lancet, Oct. 8, 2005, 366:1279-89.

Dubey et al., "Pioglitazone attenuates hypertension and inhibits growth of renal arteriolar smooth muscle in rats," American Physiological Society, 1993, R726-R732.

Duckworth et al., "Glucose control and vascular complications in veterans with type 2 diabetes," The New England Journal of Medicine, Jan. 8, 2009, 360:129-139.

Ervinna et al., "Anagliptin, a dpp-4 inhibitor, suppresses proliferation of vascular smooth muscles and monocyte inflammatory reaction and attenuates atherosclerosis in male apo e-deficient mice," Endocrinology, Mar. 2013, 145(3):1260-1270.

Extended European Search Report issued in EP Application No. 08742225.9, dated Oct. 15, 2010, 12 pages.

Extended European Search Report issued in EP Application No. 08768002.1, dated Jul. 8, 2010, 7 pages.

Final Office Action issued in U.S. Appl. No. 12/077,552, dated Oct. 22, 2014, 22 pages.

Final Office Action issued in U.S. Appl. No. 12/077,552, dated Jul. 16, 2013, 13 pages.

Final Office Action issued in U.S. Appl. No. 12/077,552, dated Apr. 10, 2012, 12 pages.

First Examination Report issued in IN Application No. 7696/DELNP/2009, dated Jan. 7, 2015, 2 pages.

First Office Action issued in CN Application No. 200880025452.8, dated Apr. 19, 2012, 11 pages (with English translation).

Fourth Office Action issued in CN Application No. 200880025452.8, dated Jan. 22, 2015, 14 pages (with English translation).

(56) References Cited

OTHER PUBLICATIONS

Fukuda et al., "Troglitazone inhibits growth and improves insulin signaling by suppression of angiotensin ii action in vascular smooth muscle cells from spontaneously hypertensive rats," Atherosclerosis, 2002, 163:229-239.
Gaziano et al., "Effect of bromocriptine-qr (a quick-release formulation of bromocriptine mesylate) on major adverse cardiovascular events in type 2 diabetes subjects," J Am Heart Assoc, 2012, 1:doi:10.1161/JAHA.112.002279, 11 pages.
Gaziano et al., "Randomized clinical trial of quick-release bromocriptine among patients with type 2 diabetes on overall safety and cardiovascular outcomes," Diabetes Care, Jul. 2010, 33:1503-1508 (12 total pages).
Gerstein et al., "Effects of intensive glucose lowering in type 2 diabetes," The New England Journal of Medicine, Jun. 12, 2008, 358:2545-59.
Gerstein, "Basal insulin and cardiovascular and other outcomes in dysglycemia," The New England Journal of Medicine, Jul. 26, 2012, 367:319-328.
Goto et al., "Exendin-4, a glucagon-like peptide-1 receptor agonist, reduces intimal thickening after vascular injury, "Biochemical and Biophysical Research Communications, 2011, 405:79-84.
Gouni-Berthold et al., "Troglitazone and rosiglitazone inhibit the low density lipoprotein-induced vascular smooth muscle cell growth," Exp Clin Endocrinol Diabetes, 2001, 109:203-209.
Ha et al., "High glucose induces connective tissue growth factor expression and extracellular matrix accumulation in rat aorta vascular smooth muscle cells via extracellular signal-regulated kinase 1 / 2," Korean J Physiol Pharmacol, Aug. 2013, 17:307-314.
Hara et al., "Central dopaminergic function in stroke prone spontaneously hypertensive rats effects of chronic treatment with lisuride on the impaired swimming ability," Database Accession No. PREV198376013141 and Folia Pharmacologica Japonica, 1982, 80(5):395-394 (Abstract only—2 pages).
Hasko et al., "Modulation of lipopolysaccharide-induced tumor necrosis factor-α and nitric oxide production by dopamine receptor agonists and antagonists in mice," Immunology Letters, 1996, 49(3):143-147.
Home et al., "Rosiglitazone evaluated for cardiovascular outcomes in oral agent combination therapy for type 2 diabetes (record): a multicentre, randomised, open-label trial," Lancet, Jun. 20, 2009, 373:2125-35.
Hsueh et al., "Insulin signaling in the arterial wall," Am J Cardiol, 1999, 84:21J-24J.
International Preliminary Report on Patentability issued in International Application No. PCT/US2008/006899, issued Dec. 1, 2009, 7 pages.
International Preliminary Report on Patentability issued in International Application No. PCT/US2008/003849, issued Oct. 6, 2009, 7 pages.
International Search Report and Written Opinion issued in International Application No. PCT/US2008/006899, dated Aug. 29, 2008, 7 pages.
International Search Report and Written Opinion issued in International Application No. PCT/US2008/003849, dated Jun. 20, 2008, 7 pages.
Kuo et al., "Hypothalamic neuropeptide Y (NPY) and the attenuation of hyperphagia in streptozotocin diabetic rats treated with dopamine D1/D2 agonists," British Journal of Pharmacology, 2006, 148:640-647.
Lan et al., "Vascular fibrosis in atherosclerosis," Cardiovascular Pathology, 2013, 22:4101-407.
Lightell et al., "Loss of canonical insulin signaling accelerates vascular smooth muscle cell proliferation and migration through changes in p27kip1 regulation," Endocrinology, Feb. 2011, 152(2):651-658.
Lusis, "Atherosclerosis," Nature, Sep. 2000, 407(6801): 233-241.
NCBI Reference Sequence XP-002587257, Hypothetical Protein BRAFLDRAFT-61678 (Branchiostoma floridae), Accession No. XP_002587257, GI No. 260784404, dated Oct. 8, 2009, (retrieved from the Internet: Feb. 23, 2015), 2 pages.
Non-final Office Action issued in U.S. Appl. No. 12/077,552, dated Sep. 15, 2015, 39 pages.
Non-final Office Action issued in U.S. Appl. No. 12/077,552, dated Feb. 10, 2014, 10 pages.
Non-final Office Action issued in U.S. Appl. No. 12/077,552, dated Jul. 7, 2011, 10 pages.
O'Neill et al., "Dopamine D2 receptor agonists protect against ischaemia induced hippocampal neurodegeneration in global cerebral ischaemia," European Journal of Pharmacology, Jul. 3, 1998, 352(1):37-46.
Office Action issued in CA Application No. 2,688,035, dated Aug. 13, 2015, 3 pages.
Office Action issued in JP Application No. 2010-510366, dated Oct. 1, 2013, 5 pages (with English translation).
Office Action issued in JP Application No. 2014-018636, dated Mar. 10, 2015, 8 pages (with English translation).
Office Action issued in MX Application No. MX/a/2009/012919, dated Sep. 19, 2011, 3 pages (with English translation).
Office Action issued in MX Application No. MX/a/2009/012919, dated Jun. 5, 2012, 6 pages (with English translation).
Office Action issued in MX Application No. MX/a/2009/012919, dated Feb. 11, 2013, 7 pages (with English translation).
Office Action issued in MX Application No. MX/a/2009/012919, dated Sep. 3, 2013, 7 pages (with English translation).
Opposition filed by Indian Pharmaceutical Alliance against corresponding Indian Patent Application No. 7696/DELNP/2009 (owned by VeroScience, LLC), Jan. 3, 2011, 38 pages.
Park et al., "The inhibition of insulin-stimulated proliferation of vascular smooth muscle cells by rosiglitazone is mediated by the akt-mtor-p70s6k pathway," Yonsei Med J, 2008, 49(4):592-600.
Patel et al., "Intensive blood glucose control and vascular outcomes in patients with type 2 diabetes," The New England Journal of Medicine, Jun. 6, 2008, 358:2560-72.
Pijl and Meinders, "Modulation of monoaminergic neural circuits: potential for the treatment of type 2 *Diabetes mellitus*," Treat Endocrine, 2002, 1(2):71-78.
Ratner et al., "Cardiovascular safety of exenatide BID: an integrated analysis from controlled clinical trials in participants with type 2 diabetes," Cardiovascular Diabetology, 2011, 10:22, 10 pages.
Schaper et al., "Peripheral vascular disease and Type 2 *Diabetes mellitus*," Diabetes Metab Res Rev, 2000, 16(Suppl 1) S11-S15.
Schobel et al, "Effects of Bromocriptine on Cardiovascular Regulation in Healthy Humans," Hypertension, 1995, 25:1075-1082.
Scirica et al., "Saxagliptin and cardiovascular outcomes in patients with type 2 *Diabetes mellitus*," The New England Journal of Medicine, Oct. 3, 2013, 369(14):1317-1326.
Second Office Action issued in CN Application No. 200880025452.8, dated Mar. 28, 2013, 15 pages (with English translation).
Stout, "Insulin as a mitogenic factor: role in the pathogenesis of cardiovascular disease," The American Journal of Medicine, Feb. 21, 1991, 90 (suppl 2A - 62S-65S).
Takasawa, "Inhibition of dipeptidyl peptidase 4 regulates microvascular endothelial growth induced by inflammatory cytokines," Biochemical and Biophysical Research Communications, 2010, 401:7-12.
Third Office Action issued in CN Application No. 200880025452.8, dated Feb. 10, 2014, 8 pages (with English translation).
Turner, "Intensive blood-glucose control with sulphonylureas or insulin compared with conventional treatment and risk of complications in patients with type 2 diabetes (UKPDS 33)," UK Prospective Diabetes Study D (UKPDS) Group, The Lancet, Sep. 12, 1998, 352:837-853.
White et al., "Alogliptin after acute coronary syndrome in patients with type 2 diabetes," The New England Journal of Medicine, Oct. 3, 2013, 369(14):1327-1335.
Zhang et al., "Inhibitory effects of bromocriptine on vascular smooth muscle cell proliferation," Atherosclerosis, 1997, 133:37-44 (Abstract only—1 page).
Zou et al., "Protein-protein coupling/uncoupling enables dopamine d2 receptor regulation of AMPA receptor-mediated excitotoxicity," The Journal of Neuroscience, Apr. 27, 2005, 25(17):4385-4395.

(56) References Cited

OTHER PUBLICATIONS

Cincotta et al., "Bromocriptine improves glycaemic control and serum lipid profile in obese Type 2 diabetic subjects: a new approach in the treatment of diabetes," *Expert Opin Investig Drugs.*, 8(10):1683-1707, Oct. 1999.

Office Action in Canadian Application No. 2,688,035, dated Aug. 13, 2015, 3 pages.

Office Action in European Application No. 08768002.1, dated Apr. 8, 2016, 4 pages.

Official Action issued in IL Application No. 202269, dated Dec. 24, 2014, 4 pages (with English translation).

Office Action issued in JP Application No. 2010-510366, dated Jun. 10, 2014, 8 pages (with English translation).

Office Action in Korean Application No. 10-2009-7027357, dated Jul. 29, 2014, 9 pages.

Office Action in Korean Application No. 10-2009-7027357, dated Jun. 29, 2015, 6 pages.

"Parlodel," Physicians' Desk Reference, Novartis Pharmaceuticals, pp. 2072-2074, Nov. 1996.

Cohn, "Nervous system control mechanisms in heart failure," Acta Medica Scandinavica, Jan. 1986, 707: 15-20.

Dutt et al., "Fatal myocardial infarction associated with bromocriptine for postpartum lactation suppression," *Aust N Z J Obstet Gynaecol.*, 38(1):116-117, Feb. 1998.

Espositi et al., "Effect of 1-5 Bromocriptine Treatment on Prolactin, Noradrenaline and Blood Pressure in Hypertensive Haemodialysis Patients", Clinical Science, Jul. 1985, 69: 51-56.

European Search Report in European Application No. 16168477.4, dated Oct. 16, 2016, 9 pages.

Francis et al., "The effects of bromocriptine in patients with congestive heart failuer," American Heart Journal, Jul. 1983, 106: 100-106.

Iffy et al., "Bromocriptine related atypical vascular accidents postpartum identified through medicolegal reviews," Med Law., 15(1):127-134, 1996.

Iffy et al., "Severe cardiac dysrhythmia in patients using bromocriptine postpartum," *Am J Ther.*, 5(2):111-115, Mar. 1998.

Katz et al., "Puerperal hypertension, stroke, and seizures after suppression of lactation with bromocriptine," *Obstet Gynecol.*, 66(6):822-824, Dec. 1985.

Laurent et al., "Expert consensus document on arterial stiffness: methodological issues and clinical applications," *Eur Heart J.*, 27(21):2588-2605, Epub Sep. 25, 2006.

McEniery et al., "Does arterial stiffness predict atherosclerotic coronary events?" *Adv Cardiol.*, 44:160-172, 2007.

Office Action in Canadian Application No. 2,693,254, dated Jan. 25, 2016, 3 pages.

Office Action in Canadian Application No. 2,693,254, dated Jun. 2, 2016, 3 pages.

Ruch et al., "Postpartum myocardial infarction in a patient receiving bromocriptine," *Obstet Gynecol.*, 74(3 Pt 2):448-451, Sep. 1989.

Zhang et al., "Inhibitory Effects of 1-5 Bromocriptine on Vascular Smooth Muscle Cell Proliferation", Atherosclerosis, Jan. 1997, 133: 37-44.

* cited by examiner

THERAPEUTIC TREATMENT FOR METABOLIC SYNDROME, TYPE 2 DIABETES, OBESITY, OR PREDIABETES

CROSS-REFERENCE TO RELATED APPLICATIONS

This application is a Continuation in Part of U.S. patent application Ser. No. 10/944,660, filed Sep. 17, 2004 now abandoned, which is a Continuation in Part of U.S. patent application Ser. No. 10/627,014, filed Jul. 25, 2003 now abandoned, which claims the benefit of Provisional Application Ser. No. 60/399,180, filed Jul. 29, 2002. This application also claims the benefit of U.S. Provisional Application Ser. No. 60/932,071, filed May 29, 2007.

BACKGROUND OF THE INVENTION

1. Field of the Invention

The present invention is directed to a method for treating the metabolic syndrome, obesity, prediabetes or metabolic conditions thereof, or Type 2 diabetes, and more particularly to a method for treating the metabolic syndrome, obesity, prediabetes or metabolic conditions thereof, or Type 2 diabetes by administering to a patient a pharmaceutical composition that increases the ratio of dopaminergic neuronal to noradrenergic neuronal activity within the central nervous system, particularly the hypothalamus of the central nervous system of the patient.

The global health crisis of obesity, diabetes and related metabolic disorders has been well established before the turn of this $21^{st}$ century. The prevalence of each of type 2 diabetes, obesity, pre-diabetes, and metabolic syndrome is reaching pandemic proportions world-wide and their prevalence is expected to continue to rise in the next two decades further exacerbating the current world wide health crisis surrounding these diseases as estimates of people diagnosed with diabetes will likely exceed 350 million globally by 2030 (Wild S, Diabetes Care, 2004, 27:1047). Diabetes and its associated co-morbidity continue to exact an exceptionally high toll on both patients and the healthcare system. In the United States, diabetes represents 11% of the US health care expenditure with cardiovascular disease accounting for approximately 20% of the annual direct medical costs for diabetes (www.diabetes.org). Despite the concerted effort to reduce cardiovascular risk factors in patients with diabetes, sixty-five percent of patients with diabetes will die from heart disease and stroke and the fact remains that type 2 diabetes increases the risk for cardiovascular disease two fold for men and three fold for women relative to gender matched individuals without type 2 diabetes (Conroy, Eur Heart J, 2003, 24: 987). The prevalence of obesity, pre-diabetes and metabolic syndrome each are also increasing world-wide with population estimates that at least double the prevalence of type 2 diabetes and each of these metabolic disorders carries a risk for cardiovascular disease, the leading cause of death in the world (Francischetti E A et al, Int J Clin Pract, 2007, 61:269; Grundy S M, Arterioscler Thromb Vasc Biol 2008, 28:629; Stein P K et al, Diabet Med 2007, 24:855). It is patently obvious that a safe and effective treatment for any and particularly all of these disorders would impart unparalleled significant benefit to humanity and that any prospect for the development of such a global therapy would be the focus of intense research and development by the healthcare industry and academia world-wide for this very reason. This invention provides a new and previously unrecognized paradigm that fills a void for the successful management of these metabolic disorders.

2. Brief Description of the Art

Obesity (commonly defined as a Body Mass Index of approximately >30 kg/m$^2$) is often associated with a variety of pathologic conditions such as hyperinsulinemia, insulin resistance, diabetes, hypertension, and dyslipidemia. Each of these conditions contributes to the risk of cardiovascular disease.

Along with insulin resistance, hypertension, and dyslipidemia, obesity is considered to be a component of the Metabolic Syndrome (also known as Syndrome X) which together synergize to potentiate cardiovascular disease. More recently, the U.S. National Cholesterol Education Program has classified Metabolic Syndrome as meeting three out of the following five criteria: fasting glucose level of at least 110 mg/dl, plasma triglyceride level of at least 150 mg/dl (hypertriglycerdemia), HDL cholesterol below 40 mg/dl in men or below 50 mg/dl in women, blood pressure at least 130/85 mm Hg (hypertension), and central obesity, with central obesity being defined as abdominal waist circumference greater than 40 inches for men and greater than 35 inches for women. The American Diabetes Association estimates that 1 in every 5 overweight people suffer from Metabolic Syndrome.

According to the guidelines of the American Diabetes Association, to be diagnosed with Type 2 diabetes, an individual must have a fasting plasma glucose level greater than or equal to 126 mg/dl or a 2-hour oral glucose tolerance test (OGTT) plasma glucose value of greater than or equal to 200 mg/dl (Diabetes Care, 26:S5-S20, 2003). A related condition called pre-diabetes is defined as having a fasting glucose level of greater than 100 mg/dl but less than 126 mg/dl or a 2-hour OGTT plasma glucose level of greater than 140 mg/dl but less than 200 mg/dl. Mounting evidence suggests that the pre-diabetes condition may be a risk factor for developing cardiovascular disease (Diabetes Care 26:2910-2914, 2003). Prediabetes, also referred to as impaired glucose tolerance or impaired fasting glucose is a major risk factor for the development of type 2 diabetes mellitus, cardiovascular disease and mortality. Much focus has been given to developing therapeutic interventions that prevent the development of type 2 diabetes by effectively treating prediabetes (Pharmacotherapy, 24:362-71, 2004).

Metabolic Syndrome (MS), also referred to as Syndrome X, is another metabolic disorder that affects other pathways and systems in the body. Originally, Metabolic Syndrome was defined as a cluster of metabolic disorders (including obesity, insulin resistance, hypertension, and dyslipidemia primarily hypertriglyceridemia), that synergize to potentiate cardiovascular disease. More recently (2001), the U.S. National Cholesterol Education Program (NCEP) has classified Metabolic Syndrome as meeting any three out of the following five criteria: fasting glucose level of at least 110 mg/dl, plasma triglyceride level of at least 150 mg/dl (hypertriglycerdemia), HDL cholesterol below 40 mg/dl in men or below 50 mg/dl in women, blood pressure at least 130/85 mm Hg (hypertension), and central obesity, with central obesity being defined as abdominal waist circumference greater than 40 inches for men and greater than 35 inches for women. Presently, there are three other internationally recognized definitions for Metabolic Syndrome as follows: 1) World Health Organization 2) American Heart Association/National Heart, Lung and blood Institute (AHA/NHLBI) and 3) International Diabetes Federation (IDF). The definitions of Metabolic Syndrome by the WHO, AHA/NHLBI and IDF are very similar to the definition of the NECP and all use the same metabolic parameters to define the syndrome, but the WHO also includes assessment of insulin fasting insulin levels (Moebus S et al, Cardiovascular Diabetology, 6: 1-10, 2007; Athyros V G et al, Int. J. Cardiology, 117: 204-210, 2007). Yet subtle differences in the thresholds for these metabolic parameters required to be classified as having the syndrome among these different definitions can result in different classification of a particular subject as having or not having the syndrome according to these different definitions. Also, the prevalence of cardiovascular disease (CVD) with MS varies by the definition used. (Moebus S et al, Cardiovascular Diabetology, 6: 1-10, 2007; Athyros V G et al, Int. J. Cardiology, 117: 204-210, 2007). Notably, none of these widely utilized definitions of MS employs vascular pro-inflammatory state, pro-coagulative state, pro-oxidant state, or endothelial dysfunction to define the syndrome. However, these non-metabolic biochemical derangements are often associated with MS. A more recent term for MS plus blood vessel pathophysiology (described just above) has been termed cardiometabolic risk. The American Diabetes Association estimates that 1 in every 5 overweight people suffer from Metabolic Syndrome.

While these disorders and diseases are related, it is clear that they have individual and distinct pathologies. For that reason, drugs used to treat one disorder (type 2 diabetes) may not be effective against another disorder (metabolic syndrome). For instance, drugs that are effective in treating Type 2 diabetes or pre-diabetes have little to no effect on effectively and safely treating Metabolic Syndrome. Additionally, certain drugs used to treat Type 2 diabetes or pre-diabetes may increase blood pressure (hypertension) or cause weight gain in the individuals taking the medication. For example, thiazolidinediones used in the treatment of Type 2 diabetes cause weight gain and has marginal effects on hypertension. Another anti-diabetic agent, metformin, also has marginal effects on hypertension and hypertriglyceridemia. Insulin, which is a hormone used to treat Type 2 diabetes can potentiate hypertension and weight gain. Moreover, anti-hypertensive drugs do not necessarily treat dyslipidemia or obesity, and many can worsen insulin sensitivity instead of improving it. It is therefore not a forgone conclusion that since a drug is an effective anti-diabetes agent, that it will be an effective treatment for metabolic and/or non-metabolic pathologies of metabolic syndrome. Since people with metabolic syndrome do not have existing disease but have a biology that portends ensuing disease, the criteria for safety are also much higher when considering a pharmaceutical agent for the treatment of this syndrome.

Since the Metabolic Syndrome is diagnosed as having several criteria (as described above) yet also encompasses vascular abnormalities such as endothelial dysfunction, vascular pro-inflammatory condition, and vascular pro-coagulative condition, the treatment of Metabolic Syndrome according to the present invention further includes a. Treatment of endothelial dysfunction associated with cardiovascular disease;
b. Treatment of hypertension, vascular pro-inflammatory state, and pro-coagulative state simultaneously. Examples of pro-inflammatory state blood markers include but are not limited to: C-reactive protein, serum amyloid A protein, interleukin-6, interleukin-1, Tumor Necrosis Factor-alpha, homocysteine, and white blood cell count. Examples of pro-coagulative state blood markers include but are not limited to: hematocrit viscosity, red cell aggregation, plasminogen activator inhibitor-1, fibrinogen, van Willebrand factor, Factor VII, Factor VIII, and Factor IX;
c. Treatment of at least two of hypertension, vascular pro-inflammatory state, or pro-coagulative state simultaneously; and
d. Treatment of at least one of hypertension, vascular pro-inflammatory state, or pro-coagulative state.

The endothelium can modify circulating factors as well as synthesize and release factors that influence cardiovascular health and disease. Endothelium dysfunction is characterized by alterations in endothelium modulation of the vasculature that favor or potentiate vasoconstriction, a pro-coagulant state, and/or a pro-inflammatory state as well as other biochemical process that all contribute to the initiation and progression of atherosclerosis (Am. J. Cardiol. 91(12A): 3H-11H, 2003; Am. J, Cardiol. 115 Suppl 8A:99S-106S, 2003) or arteriosclerosis (Nigam A et al, Am. J. Cardiol. 92: 395-399, 2003; Cohn J N et al, Hypertension 46:217-220, 2005; Gilani M et al, J. Am. Soc. Hypertens 2007).

A significant complicating issue in the treatment of metabolic disorders is that the individual pathologies of Metabolic Syndrome differ in their nature and magnitude whether presented alone or as part of the syndrome because the pathologies of the syndrome tend to synergize to produce increased risk of morbidity and mortality (Reviewed in G M Reaven, Diabetes, Obesity, and Metabolism, 4: (Suppl. 1) S13-S-18, 2002). In other words, a Metabolic Syndrome subject carries a different increased risk of cardiovascular disease as a result of his/her hypertension than does a hypertensive subject without Metabolic Syndrome. Currently, the U.S. Food and Drug Administration has not approved the use of any drug for the treatment of Metabolic Syndrome. The current definition of Metabolic Syndrome by the NCEP other definitions as described above relates to metabolic derangements and does not include aspects of non-metabolic biochemical pathology associated with the Syndrome such as pro-coagulative state, pro-inflammatory state, pro-oxidant state, or endothelial dysfunction. Yet these non-metabolic biochemical derangements contribute significantly to cardiovascular disease by mechanisms that do not necessarily involve lipid deposition and its attendant consequences of plaque formation in the intimal and inner media vessel walls (i.e., atherosclerosis). Rather, these non-metabolic biochemical abnormalities can potentiate a process that leads to a different type of vascular damage termed arteriosclerosis (defined as thickening and stiffening of the vessel wall) that can have devastating consequences on vascular health and potentiate vascular disease such as large vessel damage, myocardial infarction, stroke, and peripheral vascular disease (Safar M E Frohlich E D (eds) Atherosclerosis, Large Arteries and Cardiovascular Risk. McEniery C M et al, Adv. Cardiol. Basel, Karger, vol. 44, pp. 160-172; Laurent S et al, Eur. Heart J., 27: 2588-2605, 2006). These non-metabolic biochemical pathologies predispose the individual to increased stiffening of the vessel wall by changing the biochemical structure and architecture within the cellular layers of the wall (i.e., extracellular matrix components such as collagen and elastin, etc.) and by changing the contractile state of the smooth muscle cells therein (Safar M E Frohlich E D (eds) Atherosclerosis, Large Arteries and Cardiovascular Risk. McEniery C M et al, Adv. Cardiol. Basel, Karger, vol. 44, pp. 160-172). Such changes can effectuate vascular damage often in a much shorter time frame than those metabolic derangements of Metabolic Syndrome predisposing to atherosclerosis. Moreover, these non-metabolic derangements can be additive to those metabolic disturbances defining the Metabolic Syndrome to exacerbate vascular disease. And, arteriosclerosis can predispose one to atherosclerosis (XX). Since arteriosclerosis often precedes and potentiates atherosclerosis, the ability to successfully treat arteriosclerosis or biochemical events leading to arteriosclerosis, on e may be able to intervene medically at an earlier time point in the chronology of CVSD and produce better clinical outcomes for the patient in the long term.

The mechanisms involving non-metabolic biochemical derangements of a vascular pro-inflammatory state, pro-oxidant state, pro-coagulative state, and endothelial dysfunction to precipitate arteriosclerosis and CVD are exceedingly complex and reviewed in much detail in Nigam A et al, Am. J. Cardiol. 92: 395-399, 2003; Cohn J N et al, Hypertension 46:217-220, 2005; and Gilani M et al, J. Am. Soc. Hypertens 2007.

Previous studies have described the utility of the dopamine agonist, bromocriptine to treat individual pathologies of insulin resistance, hypertension, hypertriglyceridemia and also to treat lipid plaques of atherosclerosis (Meier A H et al, Diabetes Reviews, 4: 464, 1996; U.S. Pat. Nos. 5,006,526 and 5,565,454). However, to our knowledge no literature are available describing the utility of bromocriptine or dopamine agonists to simultaneously treat metabolic derangements of MS and non-metabolic derangements associated with MS or to simultaneously treat several non-metabolic derangements associated with MS or to treat arteriosclerosis (as opposed to atherosclerosis) or to reduce actual adverse cardiovascular events such as myocardial infarction or stroke or peripheral vascular disease. Moreover, although timing of administration to effectuate improvements in metabolic derangements such as type 2 diabetes and insulin resistance has been described (U.S. Pat. Nos. 6,004,972; 5,866,584; 5,756,513; and 5,468,755), such import of circadian timing to maximize the benefit of dopamine agonist therapy upon non-metabolic biochemical activities predisposing to arteriosclerosis and CVD that are wholly different from those metabolic influences as previously described in the literature, have not been delineated. In fact, the available literature indicate that dopamine agonist therapy such as bromocriptine is associated with increased adverse cardiovascular events such as myocardial infarction, stroke, and cerebrovascular accident (Ruch A et al, Obstet Gynecol 74: 448-451, 1989; Iffy L et al, Med Law 15: 127-134, 1996; Katz M et al, Obstet Gynecol 66: 822-824, 1985; Iffy et al, Am J Ther 5: 111-115, 1998; Ddutt S et al, Aust N Z J Obstet Gynaecol 38: 116-117, 1998). In fact, the effect of dopamine agonists such as bromocriptine to increase these adverse cardiovascular events was serious enough for the U.S. Food and Drug Administration to place a warning on the labels for these pharmaceutical dopamine agonists stating that their use has been associated with increases in hypertension, stroke, cerebrovascular accidents, and myocardial infarction (Physicians Desk Reference, Parlodel Package Insert). In stark contradistinction to this described relationship between increased dopamine agonist exposure and increased vascular disease, the current invention demonstrates that if the dopamine agonist therapy is used at the appropriate dosage and at the appropriate time of day so that its levels are not elevated throughout a greater portion of the day but are confined to a discrete daily interval of the day that approximates the natural daily circadian peak of central nervous system dopaminergic activity in healthy individuals without either vascular disease or increased levels of metabolic or non-metabolic biomarkers of vascular disease and given to a subject in need of treatment for cardiovascular disease, then dopamine agonist therapy actually decreases vascular disease and adverse vascular events, not increases them. Such daily timing of dopamine agonist within the present invention to improve arteriosclerosis biomarkers, arteriosclerosis, and CVD events also is at a time of day to reduce exaggerated increases in central noradrenergic tone that potentiate these vascular disorders. And, these beneficial vascular effects of timed dopamine agonist therapy are not the result of influences to markedly reduce hyperglycemia, plasma triglyceride levels, or blood pressure (see examples below).

The vascular endothelium is a dynamic tissue, responding to the humoral milieu it is bathed in to impact vascular architecture, and blood vessel contractile tone. Endothelial dysfunction may be defined as a biochemical state wherein the endothelium potentiates vasoconstriction, inflammation of the vessel wall intima and media layers, and physical restructuring of the extracellular matrix of the vessel wall to potentiate wall thickening and stiffening. Among the humoral factors known to stimulate biochemical endothelial dysfunction, increases in pro-inflammatory factors such as monocyte chemoattractant protein-1 (MCP-1), tumor necrosis factor-alpha (TNFalpha), interleukin-6 (IL-6) and C-reactive protein (CRP) all stimulate endothelial changes that facilitate inflammation at the vessel wall that in turn potentiate vessel wall stiffening. Moreover, decreases in plasma adiponectin, an anti-inflammatory factor at the vessel wall, also facilitate endothelial dysfunction and inflammation at the endothelium thereby potentiating vessel wall stiffening (i.e., arteriosclerosis). Vascular inflammation is coupled to and facilitates arterial stiffness (Yasmin M C et al, Arterioscler. Thromb. Vasc. Biol. 24: 969-974, 2004; Duprez D A et al, J. Hum. Hypertens. 19: 515-519, 2005; Booth A et al, Arthritis Rheum. 50: 581-588, 2004).

Vascular oxidative stress can also contribute to arterial wall stiffness. Increases in oxidative stress that produce reactive oxygen species (ROS) can scavenge nitric oxide, a potent endothelium stimulus for vasodilatation and normal endothelium function. Reduced vascular nitric oxide (NO) availability can potentiate arterial wall stiffness and a direct correlation between arterial stiffness and endothelial function has been observed in both the coronary and peripheral circulations (Wilkinson I B et al, Circulation 105: 213-217, 2002; Schmitt M et al, Hypertension 46: 227-231, 2005; Ichigi Y et al, J. Am. Coll. Cardiol. 45: 1461-1466, 2005; Ceravolo R et al, J. Am. Coll. Cardiol. 41: 1753-1758, 2003). Endothelial dysfunction and reduced NO availability can derive from too little NO synthase activity or from a consequence of over-active but "uncoupled" NO synthase activity. Paradoxically, vascular NO synthase expression may be increased in states of endothelial dysfunction and vascular disease. In the consequence of increased uncoupled vascular NO synthase activity, the enzyme functions to generate increased ROS and protein tyrosine nitration in the vessel wall while reducing the amount of available NO that collectively potentiate vascular arterioscleosis (Upmacis R K et al, Am. J. Physiol. 293: H2878-2887, 2007; Ginnan R et al, Free Radic. Biol. Med., Jan. 22, 2008; Landmesser et al, J. Clin. Invest., 111: 1201-1209, 2003; Munzel T et al, Arterioscler. Thromb. Vasc. Biol., 25: 1551-1557, 2005). Beyond their influence on inflammation, the above described adipokines (increased TNFalpha and MCP-1 and decreased adiponectin) and increased CRP, also may potentiate increases in ROS and protein nitration via perturbations of endothelial function and NO synthase (Rong L et al, Am. J. Physiol. 293: E1703-E1708, 2007; De Keulenger G W et al, Biochem. J. 329: 653-657, 1998). Increases in vessel endothelial NO synthase (eNOS) (Kagota S et al, Life Sciences 78:1187-1196, 2006) and inducible NO synthase (iNOS) are observed in older SHR rats that have increased arterial stiffness (Safar M E, In: Swales J D ed., Textbook of Hypertension, London UK: Blackwell Scientific; 1994:85-102). In the case of increased "uncoupled" NO synthase activity, the uncoupled NO synthase actually produces increased local amounts of superoxide while reducing its NO production thereby contributing to arteriosclerosis and this occurrence appears to be particularly accentuated in diabetes (Alp N J et al, J. Clin. Invest. 112: 725-735, 2003) and may contribute significantly to the arteriosclerosis of diabetes and the consequent increase in cardiovascular events (MI, stroke, and peripheral vascular damage) of diabetes versus non-diabetes subjects. A key hallmark of eNOS uncoupling is an increase in eNOS level or activity with a concurrent decrease in soluble guanyl cyclase level or activity in the endothelium as this enzyme is activated by NO to induce NO beneficial effects on the vasculature.

A pro-coagulative state also can predispose one to increased cardiovascular events. Respecting acute coronary syndrome, acute myocardial infarction, and thrombotic stroke, a critical player in their genesis is a pro-coagulative state, a condition potentiating an increase in the balance between blood clot formation and blood clot dissolution favoring blood clot formation. A pro-coagulative state involves many biochemical factors within the physiology of the body and increases in factors that potentiate blood clot formation and/or inhibit blood clot dissolution can function not only to precipitate an acute CVD event, but also can function to facilitate mechanisms involved in arteriosclerosis as well. Endothelin-1, is an example of such a factor. Endothelin-1 is an endothelium derived factor that is very pro-coagulative and that also functions as a potent vasoconstrictor that can potentiate endothelial dysfunction (Halim A et al, Thromb REs 72: 203-209, 1993; Iwamoto T et al, Nephron 73: 273-279, 1996) and thereby lead to arterial stiffness. Various factors in clot formation such as reactive platelets, plasminogen activator inhibitor-1, and fibrinogen, synergize to alter the endothelium and vessel wall in chronic hyper-coagulative states that can lead to vessel wall restructuring, chronic vasoconstriction and arteriosclerosis.

Endothelial dysfunction as described above may be defined as a biochemical state wherein the endothelium potentiates vasoconstriction, inflammation of the blood vessel wall intima and media layers, and physical restructuring of the extracellular matrix of the blood vessel wall to potentiate wall thickening and stiffening. As such, endothelial dysfunction as defined herein is a potent contributor to arterioscleosis and CVD (Nigam A et al, Am. J. Cardiol. 92: 395-399, 2003; Cohn J N et al, Hypertension 46:217-220, 2005; Gilani M et al, J. Am. Soc. Hypertens 2007). This is an important distinction because those biochemical derangements that affect arteriosclerosis versus atherosclerosis will have distinct beneficial impacts on CVD outcomes. Arteriosclerosis is often a very early sign of later CVD events long before any atherosclerosis is detectable (Nigam A et al, Am. J. Cardiol. 92: 395-399, 2003; Cohn J N et al, Hypertension 46:217-220, 2005; Gilani M et al, J. Am. Soc. Hypertens 2007). Therefore it may be possible to prophylacticly treat one with signs of arteriosclerosis such as endothelial dysfunction, a pro-inflammatory state, a pro-coagulative state, or a pro-oxidant state, which are all easily assessable clinically, in an effort to best prevent the onset of CVD by attacking the problem at its earliest warning signs. There are several simple tests to measure endothelial dysfunction, a vascular pro-inflammatory state, a pro-coagulative state, and a pro-oxidant state. Also, there are several available test to assess presence and degree of arteriosclerosis. It is also true that certain other biochemical derangements within the endothelium may also predispose one to atherosclerosis, however, as it relates to this invention, and as it is defined herein, endothelial dysfunction is a factor that potentiates arteriosclerosis. It can be appreciated that endothelial dysfunction will be characterized by biochemical derangements including but not limited to increased "uncoupled" inducible NO synthase, "uncoupled" endothelial NO synthase, increased ROS, increased production of and exposure to vasoconstrictive factors such as Endothelin-1, and increased pro-inflammatory and pro-coagulative factors.

The metabolic derangements that define the metabolic syndrome as described above differ in their impact on CVD from the non-metabolic derangements described above. Statins, drugs that reduce total and low-density lipoprotein (LDL) cholesterol synthesis by inhibiting HMG-CoA reductase activity and fibrates that reduce plasma triglyceride levels have been shown to reduce blood vessel plaques and CVD events (Colhoun H et al, Lancet 364; 685-696, 2004). Also, anti-hypertensive medications have been shown to reduce CVD events (Sever P et al, Lancet 361: 1149-1158, 2003). However, cardiovascular disease still remains the leading cause of morbidity in the world today and in subjects with type 2 diabetes cardiovascular disease is the leading cause of death. Moreover, in this diabetes patient population, CVD events have been increasing in recent years despite the availability of statins, fibrates and anti-hypertensive medications (Roglic G et al, Diabetes Care, 28: 2130-2135, 2005). Clearly these medications are not completely effective and new methods of preventing CVD and treating CVD are needed. Particularly, an effective treatment for the metabolic pathologies of metabolic syndrome and non-metabolic pathologies associated with metabolic syndrome to effectuate a prevention of, improvement in, reduction of the progression of, or regression of arteriosclerosis and CVD is needed. Methods that reduce arteriosclerosis as well as atherosclerosis and biological potentiators of both these vascular disorders are also needed. Moreover, these methods are particularly needed in subjects with type 2 diabetes. The present invention is believed to be an answer to these needs.

A variety of treatments are available for Metabolic Syndrome, obesity, Type 2 Diabetes, and pre-diabetes and related disorders. For example, U.S. Pat. No. 6,506,799 discloses methods of treating cardiovascular diseases, dyslipidemia, dyslipoproteinemia, and hypertension comprising administering a composition comprising an ether compound.

U.S. Pat. No. 6,441,036 discloses fatty acid analogous which can be used for the treatment and/or prevention of obesity, fatty liver and hypertension.

U.S. Pat. No. 6,410,339 discloses use of cortisol agonist for preparing a system for diagnosis of the Metabolic Syndrome and related conditions as belly fatness, insulin resistance including increased risk of developing senile diabetes, i.e., diabetes type II, high blood fats and high blood pressure, in which system the dose of cortisol agonist is in an interval where a difference is obtained in the inhibitory effect of the autoproduction of cortisol in individuals suffering from the Metabolic Syndrome, compared to normal values.

U.S. Pat. No. 6,376,464 discloses peptides and peptide analogues that mimic the structural and pharmacological properties of human ApoA-I. The peptides and peptide analogues are useful to treat a variety of disorders associated with dyslipidemia.

U.S. Pat. No. 6,322,976 discloses, among other things, methods of diagnosing a disease associated with a defect in insulin action, glucose metabolism, fatty acid metabolism, and/or catecholamine action by detecting a mutation in the CD36 gene.

U.S. Pat. No. 6,197,765 discloses a treatment for metabolic syndrome (syndrome-X), and resulting complications, by administration of diazoxide.

U.S. Pat. No. 6,166,017 discloses a method for the medical treatment of diabetes mellitus type II and for counteracting the risk factors forming part of the Metabolic syndrome by administration of ketoconazole.

U.S. Pat. No. 6,040,292 discloses methods for the treatment of diabetes mellitus, including type I, type II, and insulin resistant diabetes (both type I and type II). The methods of the invention employ administration of rhIGF-I/IGFBP-3 complex to a subject suffering from the symptoms of diabetes mellitus. Administration of rhIGF-I/IGFBP-3 to a subject suffering from the symptoms of diabetes mellitus results in amelioration or stabilization of the symptoms of diabetes.

U.S. Pat. No. 5,877,183 discloses methods for the regulation and modification of lipid and glucose metabolism, but not metabolic syndrome, by administering to a subject a dopamine D1 agonist, optionally in combination with a dopamine D2 agonist, an alpha-1 adrenergic antagonist, an alpha-2 adrenergic agonist, or a serotonergic inhibitor, or optionally in combination with a dopamine D2 agonist coadministered with at least one of alpha-1 adrenergic antagonist, an alpha-2 adrenergic agonist, or a serotonergic inhibitor, and further administering the subject a serotonin $5HT_{1b}$ agonist. It is well known that dopamine agonists function to both activate and deactivate dopamine receptors and thereby reduce dopaminergic neuronal activity.

U.S. Pat. No. 5,741,503 discloses methods for regulating or ameliorating lipid metabolism which comprise administration or timed administration of inhibitors of dopamine beta hydroxylase (DBH). However, the focus of this technology is reduction in noradrenergic activity level only and does not increase dopaminergic neuronal activity inasmuch as DBH is not present in dopaminergic neurons that are anatomically distinct from noradrenergic neurons where DBH resides.

In addition, several U.S. patents disclose use of dopamine agonists such as bromocriptine for use in treating pathologies relating to Type II diabetes. See, for example, U.S. Pat. Nos. 6,855,707; 6,004,972; 5,866,584; 5,756,513; and 5,468,755. Also, bromocriptine has been employed to treat type 2 diabetes or insulin resistance (Pijl H, et al Diabetes Care, 23:1154, 2000; Meier A H et al, Diabetes Reviews, 4: 464, 1996). However, dopamine agonists such as bromocriptine that are dopamine D2 receptor agonists are capable of stimulating pre-synaptic and post-synaptic dopamine receptors. Stimulation of pre-synaptic dopamine receptors with dopamine D2 receptor agonists such as bromocriptine results in marked decreased dopamine release and decreased post-synaptic dopamine binding and activity (i.e., decreased dopaminergic neuronal activity as defined herein) that is the opposite of the effect of dopamine D2 receptor agonist binding to post-synaptic dopamine receptors. Therefore, it was uncertain for some time of how bromocriptine is actually working to improve insulin resistance via interactions with dopamine receptors (i.e., it could not definitively be ascertained if it is the increasing or decreasing dopaminergic neuronal activity that is primarily responsible for the elicitation of its effects). No data were available that definitively answered the question of how bromocriptine, acting as a dopamine agonist, impacted overall dopaminergic neuronal activity. Moreover, it has been demonstrated in the scientific literature that dopamine receptor agonists are capable of improving metabolic disease (Cincotta A H et al, Exp Opin Invest Drugs, 1999, 10:1683) and worsening metabolic disease (Americ S P et al, J Pharmacol Exp Ther, 1984, 228:551; Schmidt M J et al, Eur J Pharmacol, 1983, 90:169; Mohamed H F et al, Life Sci, 1985, 36:731; Durant S, Rev Diabet Stud, 2007, 4:185; e1-Denshart et al, Life Sci, 1987, 40:1531). Likewise, dopamine receptor antagonists have been shown to improve and worsen metabolic disorders (Hajnal et al, Neuroscience, 2007, 148:584; Baptista T et al, Brain Res, 2002, 957: 144) and drugs that lower synaptic dopamine such as rimonabant reduce obesity and dysglycemia (Wright S H et al, Curr Atheroscler Rep, 2008, 10:71). Respecting body weight, dopamine receptor agonists and antagonists both have been employed to reduce feeding and dopamine ligand-receptor binding is associated with both stimulation and inhibition of feeding in different areas of the brain (Hajnal et al, Neuroscience, 2007, 148:584; Szczypka M S et al, Nat Genet, 2000, 25:102; Roseberry A G et al, J NeuroSci, 2007, 27: 7021). Dopamine agonist-receptor binding has also been coupled to increases in blood glucose level and decreases in blood glucose level (Cincotta A H et al, Exp Opin Invest Drugs, 1999, 10:1683; Americ S P et al, J Pharmacol Exp Ther, 1984, 228:551; Schmidt M J et al, Eur J Pharmacol, 1983, 90:169; Mohamed H F et al, Life Sci, 1985, 36:731; Durant S, Rev Diabet Stud, 2007, 4:185). Clearly our understanding of dopamine neurochemistry and neurophysiology involved in the regulation of fuel metabolism has been incomplete and in need of improvement. Moreover, dopamine receptor binding particularly post-synaptic dopamine D1 and D2 receptor agonist binding to their respective receptor sites is susceptible to ligand-induced desensitization (loss of ligand-receptor induced signal transduction and post-synaptic cellular effect such as effect on neuronal action potential or neurotransmitter release), compensation (post-synaptic dopamine receptor number reduction or down-regulation), and counteraction (loss of post-synaptic ligand-receptor effect and/or in certain cases reduction of endogenous neurotransmitter [i.e., dopamine] in the synapse by any means). (Ng G Y et al, Eur J Pharmacol, 1994, 267:7; Lin C W, J Pharmacol Exp Ther, 1996, 276:1022; Ng G Y et al, Proc Natl Acad Sci U.S.A., 1995, 92:10157; So C H et al, Mol Pharmacol, 2007, 72: 450; Ariano M A, Synapse, 1997, 27: 313; Namkung Y et al, J Biol Chem, 2004, 279: 49533; Amar S et al, Int J Nueropsychopharmacol, 2008, 11: 197; Morris S J et al, Eur J Pharmacol, 2007, 577: 44; Cho D I et al, Biochem Biophy Res Commun, 2006, 350: 634; Kim K M et al, J Biol Chem, 2001, 276: 37409; Barton A C et al, Mol Pharmacol, 1991, 39: 650). Dopamine D2 receptor agonists cause a reduction in synaptic dopamine level as evidenced by reductions in dopamine metabolites, DOPAC and HVA (Feenstra M G et al, Naunyn Schmiedebergs Arch Pharmacol, 1983, 324: 108; Pagliari R et al, J Neural Transm Gen Sct, 1995, 101: 13; Kendler K S et al, Life Sci, 1982, 30: 2063) and this effect, in and of itself, is counter to the intent of this invention. Desensitization and/or counteraction preclude effectiveness of dopamine agonists to produce maximized long-term increased dopamine neuronal activity with their sustained use. For example, it has been shown that treatment of subjects with type 2 diabetes for sustained periods of time with the dopamine D2 receptor agonist, bromocriptine, can result in a loss of the maximum anti-diabetes effect of such treatment over time relative to the baseline glycemic control level for these treated subjects (Cincotta A H et al, Exp Opin Invest Drugs, 1999, 10:1683). An aspect of this invention is a method of circumventing or attenuating this desensitization to dopamine D2 receptor agonist administration in the treatment of metabolic disorders. Endogenous dopamine release at appropriate levels appears to be less likely to induce these counter, desensitizing effects versus post-synaptic dopamine receptor stimulation with certain dopamine receptor agonists. Also, such endogenous dopamine is capable of binding to all post-synaptic dopamine receptors (D1, D2, D3, D4, D5) that can be more favorable versus dopamine receptor ligand binding to a single specific dopamine receptor site type (e.g., only D2). Understanding the nature of the involvement of dopaminergic neuronal activity within the central nervous system in regulation of metabolism will allow for the development of methods to better treat metabolic disorders. We have now discovered that increasing dopaminergic neuronal activity (as defined herein) produces a favorable influence on metabolic disorders. And, methods to circumvent or reduce desensitization, compensation and counteraction of dopamine receptor agonist administration that may under certain circumstances increase dopaminergic neuronal activity (namely avoiding dopamine D1 or D2 receptor agonist use or employing their use at low dosages that elicit either no or not better than modest [less than 50% of maximal response] metabolic responses) will improve the effectiveness of these methods to reduce metabolic disorders and make such approaches practical for long term use. For an example, it has now been found that it is possible to increase the effectiveness (benefit/adverse effect ratio) of dopamine D1 or D2 receptor agonists to reduce metabolic disorders by actually reducing the dose of these agents to ineffective levels and combining them with agents that increase synaptic dopamine level and/or agents that decrease norepinephrine neuronal activity (i.e, induction of synergism). That is, by directing treatment strategies for metabolic disorders towards increasing dopaminergic neuronal activity rather than towards dopamine agonist-dopamine receptor interaction per se, to effectuate a particular neurophysiology as defined herein, one can more effectively reduce metabolic disorders. Therefore any combination of dopamine receptor agonists and/or antagonists that ultimately results in an increase in dopaminergic neuronal activity can be used to reduce metabolic disorders and is in part the basis of this invention. Contrariwise, and equally importantly, use of any combination of dopamine receptor agonists and/or antagonists that ultimately does not result in an increase in dopaminergic neuronal activity cannot be used to effectively treat metabolic disorders. Specific methods to increase dopaminergic neuronal activity by utilizing specific dopamine receptor agonists and antagonists and other dopamine neuromodulators are described below. A key aspect of these said methods is to insure that synaptic dopamine levels are maintained or increased but never chronically reduced (whether said method involves administration of post-synaptic dopamine receptor agonists or not) to produce beneficial effects on metabolic disorders.

Similarly, norepinephrine ligand-binding functions produce a wide array of physiological responses depending upon which particular receptor site is bound and also depending upon which neuronal center is impacted. For example, pharmacological interventions that act to induce increases in central norepinephrine release and synaptic levels have been shown to stimulate weight loss and treat obesity, however increased central norepinephrine levels have been associated with obesity, insulin resistance and diabetes (Astrup A et al, Obesity, 2008, March 20:Epub; Gadde K M et al, Expert Rev Neurother, 2007, 7:17). Drugs that stimulate norepinephrine release or increase synaptic norpeinephrine level have been employed to treat obesity and have had limited success due to modest efficacy and adverse side-effects such as hyperactivity, hypertension, valvular heart disease, and increased heart rate (Ioannides-Demos L L et al, Drug Saf, 2006, 29:302; Florentin M et al, Obesity Rev, 2007, Nov. 23: Epub).

There are pharmaceutical agents that are classified as dopamine/norepinephrine reuptake inhibitors such as bupropion, mazindol, sibutramine, and methylphenidate to name but a few examples, that function to block the neuronal reuptake of synaptic dopamine and norepinpehrine and consequently increase both dopaminergic and noradrenergic neuronal activities (as defined herein—see below). These dopamine/norepinephrine reuptake inhibitors have been shown to produce beneficial effects on obesity and to some extent on diabetes as well. However, the effects of these dopamine/norepinephrine reuptake inhibitors are modest in all cases and are associated with untoward side-effects such as increased heart rate and hypertension. Likewise, agents that stimulate the concurrent neuronal release of dopamine and norepinephrine have produced modest positive yet very mixed results on obesity and diabetes and concurrent serious side effects. The untoward side effects of the dopamine/norepinephrine reuptake inhibitors and the dopamine/norepinephrine release enhancers also limit the dose that can be administered to the patient and consequently can limit the magnitude of any benefit on metabolic disorders as well. Contrariwise, the present invention provides an opposite method of treating metabolic disease from that of these dopamine/norpeinephrine reuptake inhibitors that employs approaches that counter-intuitively improve the effects of dopamine/norepinephrine reuptake inhibitors by actually inhibiting the effects of these agents. Methods of the present invention act to block the effects of increasing synaptic norepinephrine from these concurrent dopamine/norepinephrine reuptake inhibitor or pre-synaptic release stimulator agents and thereby improve metabolism. Such an approach also reduces the untoward side-effects of the dopamine/norepinephrine reuptake inhibitors or release enhancers. Likewise, dopamine beta hydroxylase inhibition has been shown to reduce norepinephrine levels and metabolic disorders, however, dopamine beta hydroxylase does not exist in dopamine neurons and therefore its inhibition cannot elicit any effect to increase dopaminergic neuronal activity and thereby produce a beneficial impact on metabolic disorders. What is needed to effectively treat metabolic disorders is a method that can increase central (central nervous system) dopaminergic neuronal activity and decrease central noradrenergic neuronal activity. We have now unexpectedly found that methods that increase dopaminergic neuronal activity and decrease norepinephrine neuronal activity interact and often synergize to reduce markedly and in sustained manner metabolic disorders and key elements thereof while minimizing adverse events.

SUMMARY OF THE INVENTION

The current invention is a novel and improved method of exploiting dopamine and norepinephrine neurophysiology and neuropathology to treat metabolic disorders such as obesity, type 2 diabetes, pre-diabetes, metabolic syndrome, cardiometabolic risk, cardiovascular disease, arteriosclerosis, and atherosclerosis, including their key elements (as defined herein—see below), that targets the induction of specific changes in neuronal activity rather than non-specific ligand-receptor interactions to produce these effects. This invention is either contrary to and the opposite of and/or wholly different from and advantageous to previous approaches that have employed methods impacting dopamine and norepinephrine neurochemistry to treat metabolic disorders. In addition, it is the first description of specific novel methods impacting dopamine and norepinephrine neurophysiology to treat several specific metabolic disorders including metabolic syndrome, cardiometabolic risk, and cardiovascular disease, and key elements thereof. Central Nervous System activity appears to play a significant role in metabolic disorders including Metabolic Syndrome, type 2 diabetes, obesity, and prediabetes and key elements of metabolic disorders. However, there are no neuronal activity-based treatments for these diseases that consider both dopaminergic and noradrenergic neuronal activity in a particular inter-related fashion. It had not been previously described that metabolic disorders including key elements of metabolic disorders could be most effectively treated by methods that increase dopaminergic neuronal activity and increase noradrenergic neuronal activity (as defined herein) that is the basis of this invention. Such methods have several distinct and unique attributes including a) the ability to synergize to reduce metabolic disorders and key elements thereof, b) allowance of lower doses of agents used to either increase dopaminergic neuronal activity or decrease noradrenergic neuronal activity to effectuate a reduction in metabolic disorders or key elements thereof thus reducing the untoward side-effects of such agents, and/or c) the minimization of desensitization, compensation or counteraction to such treatment. What is needed in the art are treatments for these diseases, disorders and key elements thereof that treat dopaminergic and noradrenergic neuronal activity in these distinct ways. The present invention is believed to be an answer to that need.

In one aspect, the present invention is directed to a method of simultaneously treating hypertension, hypertriglyceridemia, a pro-inflammatory state, and insulin resistance associated with Metabolic Syndrome, the method comprising the step of administering to a patient suffering with Metabolic Syndrome a therapeutically effective amount of a pharmaceutical preparation use of which increases the central neuronal dopamine activity and/or decreases central neuronal norepinephrine activity to simultaneously treat hypertension, hypertriglyceridemia, a pro-inflammatory state, and insulin resistance.

In another aspect, the present invention is directed to a method for simultaneously treating hypertension, hypertriglyceridemia, a pro-inflammatory state, a pro-coagulative state, and insulin resistance associated with the Metabolic Syndrome, the method comprising the step of administering to a patient suffering from Metabolic Syndrome a therapeutically effective amount of a pharmaceutical preparation use of which increases the central neuronal dopamine activity and/or decreases central neuronal norepinephrine activity to simultaneously treat hypertension, hypertriglyceridemia, a pro-inflammatory state, a pro-coagulative state, and insulin resistance.

In another aspect, the present invention is directed to a method for simultaneously treating hypertension, a pro-inflammatory state, a pro-coagulative state, and a pro-oxidant state associated with the Metabolic Syndrome, the method comprising the step of: administering to a patient suffering from Metabolic Syndrome a therapeutically effective amount of a pharmaceutical preparation use of which increases the central neuronal dopamine activity and/or decreases central neuronal norepinephrine activity to simultaneously treat hypertension, a pro-inflammatory state, a pro-coagulative state, a pro-oxidant state, and any combination thereof. A pro-oxidant state is defined as a biochemical milieu of increased reactive oxygen species or reactive nitrogen species at the tissue level.

In another aspect, the present invention is directed to a method for simultaneously treating hypertension, a pro-inflammatory state, and a pro-coagulative state the method comprising the step of: administering to a patient suffering from hypertension, a pro-inflammatory state, and a pro-coagulative state, a therapeutically effective amount of a pharmaceutical preparation use of which increases the central neuronal dopamine activity and/or decreases central neuronal norepinephrine activity to simultaneously treat hypertension, a pro-inflammatory state, a pro-coagulative state, a pro-oxidant state, and any combination thereof.

In another aspect, the present invention is directed to a method for treating at least one of hypertension, a pro-inflammatory state, and a pro-coagulative state, or a pro-oxidant state associated with the Metabolic Syndrome, the method comprising the step of administering to a patient suffering from Metabolic Syndrome or not, a therapeutically effective amount of a pharmaceutical preparation use of which increases the central neuronal dopamine activity and/or decreases central neuronal norepinephrine activity to treat at least one of hypertension, a pro-inflammatory state, a pro-coagulative state, and a pro-oxidant state.

In another aspect, the present invention is directed to a method for treating at least two of hypertension, a pro-inflammatory state, and a pro-coagulative state the method comprising the step of administering to a patient suffering from at least one of hypertension, a pro-inflammatory state, and a pro-coagulative state, a therapeutically effective amount of a pharmaceutical preparation use of which increases the central neuronal dopamine activity and/or decreases central neuronal norepinephrine activity to treat at least two of hypertension, a pro-inflammatory state, and a pro-coagulative state.

In another aspect, the present invention is directed to a method for treating endothelial dysfunction associated with the Metabolic Syndrome, the method comprising the step of administering to a patient suffering from Metabolic Syndrome or not a therapeutically effective amount of a pharmaceutical preparation use of which increases the central neuronal dopamine activity and/or decreases central neuronal norepinephrine activity to treat endothelial dysfunction.

In another aspect, the present invention is directed to a method for treating endothelial dysfunction associated with cardiovascular disease, the method comprising the step of administering to a patient suffering from endothelial dysfunction, a therapeutically effective amount of a pharmaceutical preparation use of which increases the central neuronal dopamine activity and/or decreases central neuronal norepinephrine activity to treat endothelial dysfunction.

In another aspect, the present invention is directed to a method for simultaneously treating hypertension, hypertriglyceridemia, a pro-inflammatory state, a pro-coagulative state, insulin resistance, a pro-oxidant state, and endothelial dysfunction associated with the Metabolic Syndrome or not, the method comprising the step of administering to a patient suffering from Metabolic Syndrome or not a therapeutically effective amount of a pharmaceutical preparation use of which increases the central neuronal dopamine activity and/or decreases central neuronal norepinephrine activity to simultaneously treat hypertension, hypertriglyceridemia, a pro-inflammatory state, a pro-coagulative state, insulin resistance, a pro-oxidant state, and endothelial dysfunction.

In another aspect, the invention is directed to a method for treating at least one of metabolic derangements consisting of insulin resistance or hypertriglyceridemia or hypertension and at least one of non-metabolic derangements consisting of a pro-inflammatory state, a pro-coagulative state, a pro-oxidant state, or endothelial dysfunction the method comprising the step of administering to a patient suffering from Metabolic Syndrome or not a therapeutically effective amount of a pharmaceutical preparation use of which increases the central neuronal dopamine activity and/or decreases central neuronal norepinephrine activity to treat at least one of metabolic derangements consisting of insulin resistance or hypertriglyceridemia or hypertension and at least one of non-metabolic derangements consisting of a pro-inflammatory state, a pro-coagulative state, a pro-oxidant state, or endothelial dysfunction.

In another aspect, the invention is directed to a method for treating at least one of non-metabolic derangements consisting of a vascular pro-inflammatory state, a pro-coagulative state, a pro-oxidant state, or endothelial dysfunction associated with metabolic syndrome or not the method comprising the step of administering to a patient suffering from Metabolic Syndrome or not a therapeutically effective amount of a pharmaceutical preparation use of which increases the central neuronal dopamine activity and/or decreases central neuronal norepinephrine activity to treat at least one of non-metabolic derangements consisting of a pro-inflammatory state, a pro-coagulative state, a pro-oxidant state, or endothelial dysfunction.

In another aspect, the present invention is directed to a method for treating, preventing, delaying, retarding or slowing the progression of arteriosclerosis the method comprising the step of administering to a patient suffering from Metabolic Syndrome or not a therapeutically effective amount of a pharmaceutical preparation use of which increases the central neuronal dopamine activity and/or decreases central neuronal norepinephrine activity to treat or prevent arteriosclerosis.

In another aspect, the present invention is directed to a method for treating, preventing, delaying, retarding or slowing the progression of vascular disease, including cardiovascular disease, myocardial infarction, cerebrovascular disease, stroke, or peripheral vascular disease comprising the step of administering to a patient in need of such treatment a therapeutically effective amount of a pharmaceutical preparation use of which increases the central neuronal dopamine activity and/or decreases central neuronal norepinephrine activity to treat such vascular disease. Surprisingly it was found that the magnitude of the beneficial effect derived from therapy with such a pharmaceutical preparation, use of which increases the central neuronal dopamine activity and/or decreases central neuronal norepinephrine activity, upon vascular disease is very large (see example 3 below) and greater than one would predict from available evidence of dopamine agonist effects on hyperglycemia or dyslipidemia or hypertension.

In another aspect, the invention relates to treating aspects of the above delineated pathologies and disorders simultaneously to treating type 2 diabetes.

In another aspect, the present invention is directed to a method of a) simultaneously treating hypertension, hypertriglyceridemia, a pro-inflammatory state, a pro-coagulative state, a pro-oxidant state, and insulin resistance, b) simultaneously treating three or more of hypertension, hypertriglyceridemia, a pro-inflammatory state, a pro-coagulative state, a pro-oxidant state, and insulin resistance, c) treating Metabolic Syndrome, d) simultaneously treating Type-2 Diabetes and Metabolic syndrome, e) simultaneously treating Type-2 Diabetes and one or more of hypertension, hypertriglyceridemia, a pro-inflammatory state, a pro-coagulative state, a pro-oxidant state, and insulin resistance, f) treating endothelial dysfunction associated with the Metabolic Syndrome or g) treating endothelial dysfunction associated with cardiovascular disease the method comprising the step of administering to a patient a therapeutically effective amount of a pharmaceutical preparation use of which increases the central neuronal dopamine activity and/or decreases central neuronal norepinephrine activity, at a first predetermined time of day. And furthermore, the present invention is directed to a method of treating the aforementioned vascular disease related conditions wherein such pharmaceutical preparation is administered in a manner to effectuate a peak in central dopaminergic neuronal activity during a discrete daily interval that approximates the time of the daily peak in hypothalamic dopaminergic activity of a healthy mammal of the same species. Moreover, the present invention is directed to a method of treating a human with the aforementioned conditions wherein the pharmaceutical preparation, use of which increases central dopamine neuronal activity and decreases central norepinephrine neuronal activity, is administered in a manner to effectuate a peak in the central level of dopamine neuronal activity during a discrete daily interval from about 0400 to 1200 hours. Also, the present invention is directed to a method of treating a human with the aforementioned conditions wherein the compound that increases central dopaminergic neuronal activity is administered in a manner to effectuate a peak in central dopaminergic neuronal activity during a discrete daily interval from about 0400 to 1200 hours.

As defined herein, the term "non-metabolic derangement" refers to biomarkers for vascular diseases, including, but not limited to, pro-inflammatory state, a pro-coagulative state, a pro-oxidant state, or endothelial dysfunction. A biomarker is further defined as a physiological condition or biological entity (molecule) that is diagnostic or predictive of increased risk of a future disease state.

As defined herein, the term "treating" includes reducing the rate of progression of, or increasing the time to onset of, a selected disease state, as well as a reduced need for revascularization surgery in a patient in need of such treatment. In another aspect, the present invention is directed to a method for treating a patient suffering from a metabolic disorder (e.g., the metabolic syndrome, Type 2 diabetes, obesity, or prediabetes, including key elements of these metabolic disorders), the method comprising the step of administering to a patient a therapeutically effective amount of a pharmaceutical preparation use of which increases the central neuronal dopamine activity and/or decreases central neuronal norepinephrine activity. In another aspect, the present invention is directed to a method for treating a patient suffering from a metabolic disorder (e.g., the metabolic syndrome, Type 2 diabetes, obesity, or prediabetes, including key elements of these metabolic disorders), the method comprising the step of increasing the ratio of dopaminergic neuronal to noradrenergic neuronal activity within the central nervous system or within the hypothalamus of the central nervous system of the patient.

The term "metabolic disorder" includes disorders associated with aberrant whole-body glucose, lipid and/or protein metabolism of a species and pathological consequences arising there from including Metabolic Syndrome, type 2 diabetes, obesity, and pre-diabetes. These metabolic disorders may or may not be associated with aberrant patterns in the daily levels (and fluctuations) of prolactin secretion.

The "key elements" of these metabolic disorders include but are not limited to, impaired fasting glucose or impaired glucose tolerance, increased waist circumference, increased fasting plasma glucose, increased fasting plasma triglycerides, decreased fasting high density lipoprotein level, increased blood pressure, insulin resistance, hyperinsulinemia, cardiovascular disease (or components thereof such as arteriosclerosis, coronary artery disease, peripheral vascular disease, or cerebrovascular disease), congestive heart failure, elevated plasma norepinephrine, elevated cardiovascular-related inflammatory factors, elevated plasma factors potentiating vascular endothelial dysfunction, hyperlipoproteinemia, arteriosclerosis or atherosclerosis, hyperphagia, hyperglycemia, hyperlipidemia, and hypertension or high blood pressure, increased plasma postprandial triglyceride or free fatty acid levels, increased cellular oxidative stress or plasma indicators thereof, increased circulating hypercoagulative state, hepatic steatosis, renal disease including renal failure and renal insufficiency.

In another aspect, the present invention is directed to a method for treating a patient suffering from the metabolic syndrome, Type 2 diabetes, obesity, or prediabetes, including key elements of these metabolic disorders comprising the step of: administering to a patient suffering from the metabolic syndrome, Type 2 diabetes, obesity, or prediabetes a pharmaceutical composition that increases the central (central nervous system) dopaminergic neuronal activity to central noradrenergic neuronal activity level ratio in the subject.

In another aspect, the present invention is directed to a method for treating a patient suffering from the metabolic syndrome, Type 2 diabetes, obesity, or prediabetes, including key elements of these metabolic disorders comprising the step of: administering to a patient suffering from the metabolic syndrome, Type 2 diabetes, obesity, or prediabetes a pharmaceutical composition comprising (1) at least one compound that stimulates an increase in central (central nervous system) dopaminergic neuronal activity level in the subject, and (2) at least one compound that stimulates a decrease in central noradrenergic neuronal activity level in the subject.

In another aspect, the present invention is directed to a pharmaceutical composition effective for treating the metabolic syndrome, Type 2 diabetes, obesity, or prediabetes, including key elements of these metabolic disorders the composition comprising: (1) at least one central dopaminergic neuronal activity activator; (2) at least one central noradrenergic neuronal activity inhibitor; and (3) a pharmaceutically acceptable carrier.

In another aspect, the present invention is directed to a pharmaceutical composition effective for treating the metabolic syndrome, Type 2 diabetes, obesity, or prediabetes, including key elements of these metabolic disorders the composition comprising at least one compound that simultaneously stimulates (1) an increase in central dopaminergic neuronal activity level, and (2) a decrease in central noradrenergic neuronal activity level, the compound selected from the group consisting of catecholamine modifiers and a pharmaceutically acceptable carrier.

These and other aspects will be described in more detail in the following detailed description of the invention.

BRIEF DESCRIPTION OF THE FIGURES

The invention will be more fully understood from the following detailed description taken in conjunction with the accompanying figures in which.

DETAILED DESCRIPTION OF THE INVENTION

Figure 1:
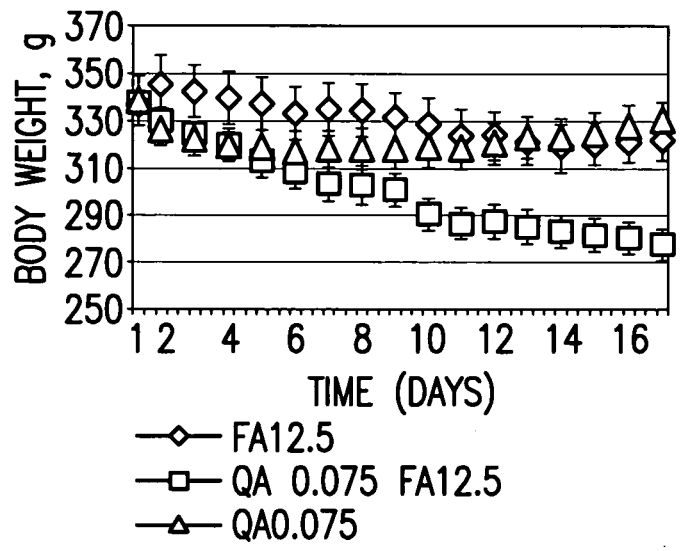
FIG. 1 is a graph showing the effect of quinelorane plus fusaric acid on body weight in SHR rats on a high fat diet.

In general, it is an object of this invention to provide additional improved methods for reducing in vertebrate subjects, including humans, in need of such treatment at least one of hyperglycemia, glycated hemoglobin A1c (HbA1c), hyperinsulinemia, glucose intolerance, insulin resistance, hypertriglyceridemia, and body fat store level. It is another object of this invention to provide additional improved methods for reducing at least one metabolic disorder (as defined herein), including type 2 diabetes, metabolic syndrome, pre-diabetes, and obesity, and including key elements of metabolic disorders (as defined herein). It is still another object of this invention to provide methods to reduce at least one of cardiometabolic risk, arteriosclerosis, and vascular, including cardiovascular, disease and its progression.

The novel treatment for metabolic disorders, including the metabolic syndrome (obesity, insulin resistance, hyperlipidemia, and hypertension), Type 2 diabetes, obesity, and/or prediabetes including key elements of metabolic disorders consists of administering to a mammalian species in need of such treatment a pharmaceutical composition that simultaneously stimulates an increase in central dopaminergic neuronal activity level (particularly within neurons innervating the hypothalamus and the hypothalamus itself) and a decrease in central noradrenergic neuronal activity level (particularly within the brain stem region that innervates the hypothalamus and the hypothalamus itself). It has been unexpectedly discovered that increasing the ratio of dopaminergic neuronal to noradrenergic neuronal activity within the central nervous system, particularly the hypothalamus of the central nervous system reduces metabolic disorders and improves the conditions associated with metabolic syndrome, type 2 diabetes, obesity, and/or prediabetes and key elements thereof. It has been surprisingly found that pharmacological methods which simultaneously both increase central dopaminergic neuronal activity and decrease central norepinephrine activity produce widespread improvements (reductions) in several metabolic disorders and to a magnitude of improvement that is broader than, superior (augmentative or potentiating) and often syngesitic relative to therapies that either increase central dopaminergic neuronal activity or decrease central norepinephrine activity. As defined herein, "neuronal activity" refers to either an increase or decrease in the action potential of a neuron. More specifically, as defined herein, "neuronal activity" refers to either an increase or decrease in the synaptic neurochemical signal transmission of a neuron to another thereby affecting action potential. More narrowly yet, as defined herein, "neuronal activity" refers to the biochemical communication to a (secondary [e.g., post-synaptic]) neuron from either the neurochemical signal transmission of another (primary [e.g., pre-synaptic]) neuron (e.g., as via an endogenous neurotransmitter) or from any neuromodulatory compound (e.g., an exogenous neurotransmitter receptor modulator such as a pharmaceutical agent) thereby affecting action potential or neurotransmitter release of the secondary neuron. As such, an increase in dopaminergic neuronal activity would be characterized by a) an increase in release of dopamine molecules from a dopamine producing (primary) neuron, an increase in dopamine molecules within the synapse by any mechanism, and/or increase in dopamine-mimetic compound(s) from any source (e.g., pharmaceutical) resulting in increased binding to dopaminergic receptor sites of other (secondary) neuron(s) that affect said other neuron(s)' action potential or neurotransmitter release in a manner consistent with increased dopamine ligand-dopamine receptor binding signal transduction (e.g., post-synaptic dopamine receptor agonist) and/or b) an increase in sensitivity or responsiveness of said "other (secondary)" neuron(s) to such dopamine or dopamine-mimetic compound(s)' ability to affect action potential or neurotransmitter release in said "other (secondary)" neuron (e.g., as an increase in dopamine receptor number or affinity or responsiveness). Contrariwise, dopamine-mimetic binding to dopamine-producing neurons (i.e., presynaptic dopamine neurons) and/or increased sensitivity or responsiveness of dopamine producing neurons to respond to neurotransmitters or neuromodulators that thereby reduces dopamine release would be considered an activity leading to a decrease in dopaminergic neuronal activity [and, when considered in and of itself, is an undesirable aspect of dopaminergic activity respecting this invention]. And, with such a definition of "neuronal activity", a decrease in noradrenergic neuronal activity would be characterized by a) a decrease in release of norepinephrine molecules from a norepinephrine producing (primary [e.g., pre-synaptic]) neuron, a decrease in norepinephrine molecules within the synapse by any mechanism, or increase in compound(s) from any source (e.g., pharmaceutical) binding to norepinephrine receptor sites of other (secondary [e.g., post-synaptic]) neuron(s) that affect said other (secondary) neuron(s)' action potential or neurotransmitter release in a manner consistent with a decrease, diminution or blockade of norepinephrine ligand-receptor binding signal transduction function (e.g., post-synaptic norepinephrine receptor antagonist) and/or b) a decrease in sensitivity or responsiveness of said "other (secondary)" neuron(s) to norepinephrine's ability to affect action potential or neurotransmitter release in said "other (secondary)" neuron (e.g., as a decrease in norepinephrine receptor ligand binding availability [e.g., receptor blockade with antagonist], or receptor number or affinity or ligand-receptor complex mediated signal transduction). Contrariwise, a decrease in norepinephrine or norepinephrine-mimetic binding to norepinephrine-producing neurons and/or decreased sensitivity or responsiveness of norepinephrine producing neurons to respond to neurotransmitters or neuromodulators that thereby increases norepinephrine release would be considered an activity leading to an increase in noradrenergic neuronal activity [and, when considered in and of itself, is an undesirable aspect of noradrenergic activity respecting this invention]. For the sake of clarity, post-synaptic dopamine receptor agonists include dopamine D1, D2, D3, D4, and D5 receptor agonists and post-synaptic norepinephrine receptor antagonists include alpha 2bc and alpha1 antagonists.

The following points describe in more detail the novel features of the present invention.

Firstly, it is not the specific neurochemical agents used to treat metabolic disease that defines the present invention but rather how to use specific neurochemicals to effectuate an increase in the central nervous system dopamine to noradrenaline neuronal activity ratio, that is, to increase central dopamine neuronal activity and decrease central norepinephrine neuronal activity and secondly to do so without inducing desensitization, compensation, or simultaneous counteraction to this effect by way of interactions at multiple neuronal sites. Important but not limiting examples of this distinguishing point include the following two cases:

(A) Dopamine D2 receptor agonists that stimulate both presynaptic and postsynaptic dopamine receptors will stimulate postsynaptic D2 receptors but will reduce presynaptic dopamine release and this will tend to counter the postsynaptic D2 stimulation. One aspect of the present invention relates to stimulating the postsynaptic D2 receptors preferentially or in combination with another agent that will counter or reduce the D2 agonist effect on presynaptic receptors (which reduces synaptic dopamine levels) consequently reducing desensitization, compensation or simultaneous counteraction to the desired increase in dopaminergic neuronal activity. As such, merely introducing or supplying a dopamine D2 receptor agonist to the subject in need of increasing the dopamine to noradrenaline activity ratio does not fully describe the present invention unless its net effect is to increase dopaminergic neuronal activity without potentiating desensitization, compensation, or concurrent dampening of the dopaminergic postsynaptic stimulation (e.g., minimizing any reduction in synaptic dopamine levels) as just described above. These are two distinct activities—D2 agonist presentation versus increasing dopaminergic neuronal activity. To further delineate this distinction of neurochemical agent versus neurochemical effect, one embodiment of the present invention is to actually use a presynaptic dopamine D2 receptor antagonist to thereby increase synaptic dopamine release [presynaptic dopamine binding to D2 receptors inhibits dopamine release] and dopaminergic neuronal activity. One could further add this presynaptic D2 receptor antagonist to a dopamine D2 postsynaptic receptor agonist to further potentiate or augment the increase in dopaminergic neuronal activity. Furthermore, to effectuate an increase in dopaminergic neuronal activity, one may combine post-synaptic dopamine receptor agonists with agents that increase synaptic dopamine levels to maximize the increase in dopaminergic neuronal activity while minimizing the dose of the post-synaptic dopamine receptor agonist and therefore the likelihood of the adverse effects of desensitization or counteraction.

(B) A second similar case is with noradrenergic alpha 2 receptor agonists. These compounds bind to postsynaptic alpha 2 sites where they function to stimulate noradrenergic neuronal activity and to presynaptic alpha 2 receptors where they function to inhibit norepinephrine release and reduce norepinephrine neuronal activity. One aspect of the present invention employs stimulation of presynaptic alpha 2 sites to reduce norepinephrine release and activity and thereby improve metabolism. Often the countering effects of a given compound for use in the present invention can be separated from the beneficial effects of the compound by merely adjusting the dose so that the desired effect is persevered at the dose utilized but not the countering or limiting effect of the compound(s).

Secondly, it is possible to use a mixed dopamine/norepinephrine reuptake inhibitor or a mixed dopamine/noradrenaline presynaptic release stimulator, that increase both dopamine and noradrenaline neuronal activity, with an agent that reduces norepinephrine neuronal activity to thereby increase the dopamine to noradrenaline neuronal activity ratio and improve metabolic disease. In this manner, one exploits the dopamine reuptake inhibition or dopamine release properties of the compound while blocking the undesirable norepinephrine reuptake or noradrenaline release properties of the compound, respectively with another agent that reduces norepinephrine neuronal activity (see Example 4 below). While data are available demonstrating the utility of dopamine/norepinephrine reuptake inhibitors in treating obesity and diabetes, the effects are limited and not clinically meaningful. The present invention corrects this shortcoming and produces a more robust effect on metabolic disease by adding a noradrenergic neuronal activity inhibitor to the mixed dopamine/norepinephrine reuptake inhibitor or mixed dopamine/noradrenaline release stimulator thus increasing the dopamine to noradrenaline neuronal activity ratio.

A more detailed description of certain examples of this aspect of this invention may be provided as follows. The present invention is directed to a method for treating a patient suffering from a metabolic disorder including the metabolic syndrome, Type 2 diabetes, obesity, or prediabetes, including key elements of these metabolic disorders comprising the steps of administering to a patient suffering from metabolic disorders, including the metabolic syndrome, Type 2 diabetes, obesity, or prediabetes including key elements of these metabolic disorders a pharmaceutical composition defined as a "dopamine/norepinephrine neuronal activity ratio-increasing therapeutic" and comprising any one of the following:

1. At least one compound that is a dopamine and norepinephrine neuronal reuptake inhibitor plus at least one other compound that produces a decrease in central norepinephrine neuronal activity by any means. Examples of dopamine and norepinephrine reuptake inhibitor compounds include bupropion, mazindol, nomifensine, tesofensine, sibutramine, and methylphenidate.

2. At least one compound that is a dopamine and norepinephrine release enhancer plus at least one compound that produces a decrease in central norepinephrine neuronal activity by any means. Examples of compounds that are dopamine and norepinephrine release enhancers are amphetamine and methamphetamine.

3. At least one compound that at a given dose is a selective dopamine reuptake inhibitor that is void of or substantially lacking of any norepinephrine reuptake inhibition at such given dose with or without at least one compound that decreases central norepinephrine neuronal activity by any means. Examples of selective dopamine reuptake inhibitors are GBR 12909, GBR 12935 and GBR 12783.

4. At least one dopamine D2 receptor agonist plus a dopamine auto-receptor antagonist with or without at least one other compound that produces a decrease in central norepinephrine neuronal activity by any means. An example of dopamine auto-receptor antagonists is AJ76.

5. At least one dopamine post-synaptic receptor agonist plus a dopamine auto-receptor antagonist with or without at least one other compound that produces a decrease in central norepinephrine neuronal activity by any means.

6. At least one compound that increases dopamine neuronal activity by acting as a stimulator of dopamine synthesis or release such as brain derived neurotrophic factor (BDNF) or L-DOPA or by acting as an inhibitor of synaptic dopamine degradation, for example such as monoamine oxidase inhibitor B (e.g., deprenyl) or dopamine monooxygenase inhibitor, or by acting as a selective dopamine reuptake inhibitor or a presynaptic dopamine autoreceptor antagonist, plus at least one other compound that produces a decrease in central norepinephrine neuronal activity by any means.

7. At least one compound that acts as a dopamine D2 receptor agonist plus a compound that increases central dopamine neuronal activity by increasing synaptic levels of dopamine with or without at least one compound that decreases central norepinephrine neuronal activity by any means.

8. At least one compound that acts as a dopamine D1 receptor agonist plus a compound that increases central dopamine neuronal activity by increasing synaptic levels of dopamine with or without at least one compound that decreases central norepinephrine neuronal activity by any means.

9. At least one compound that acts as a post-synaptic dopamine receptor agonist plus a compound that increases central dopamine neuronal activity by increasing synaptic levels of dopamine with or without at least one compound that decreases central norepinephrine neuronal activity by any means.

10. At least one compound that is a dopamine D1 or D2 receptor agonist plus at least one compound that decreases central norepinephrine neuronal activity by acting as an inhibitor of norepinephrine synthesis, for example a dopamine beta hydroxylase inhibitor, or release or by decreasing synaptic levels of norepinephrine by acting as a stimulator of norepinephrine reuptake or stimulator of cellular or synaptic norepinephrine degradation.

11. At least one compound that increases central dopamine neuronal activity by any means plus at least one compound that decreases central norepinephrine neuronal activity by acting as an inhibitor of norepinephrine synthesis or release, for example a dopamine beta hydroxylase inhibitor, or by decreasing synaptic levels of norepinephrine by acting as a stimulator of norepinephrine reuptake or stimulator of pre-synaptic cellular or synaptic norepinephrine degradation.

12. At least one compound that decreases central noradrenergic neuronal activity by any means and/or at least one compound that increases central dopaminergic neuronal activity by any means other than by acting as a dopamine D1 or D2 receptor agonist.

13. At least one compound that is a dopamine D1 or D2 receptor agonist administered at doses that elicit no or less than half maximal effects to reduce metabolic disorders plus at least one compound that decreases central noradrenergic neuronal activity by any means.

14. At least one compound that increases central synaptic dopamine levels from a presynaptic dopaminergic neuron and at least one compound that decreases central norepinephrine neuronal activity.

15. At least one compound that decreases central norepinephrine neuronal activity by decreasing synaptic norepinephrine levels from a presynaptic noradrenergic neuron and at least one compound that increases central dopaminergic neuronal activity without causing desensitization or counteraction.

16. At least one compound that is not a dopamine D1 or D2 agonist that increases central dopaminergic neuronal activity and/or at least one compound that decreases central norepinephrine neuronal activity.

17. At least one compound that increases central dopaminergic neuronal activity and/or at least one compound that decreases central norepinephrine neuronal activity.

The above 17 methods are all examples of neurophysiological means of increasing the dopaminergic to noradrenergic neuronal activity ratio in the central nervous system, particularly in the hypothalamus. Any compound(s) or combination of compounds, as the case may be, that produce the mentioned neuronal activity effects listed in any of the above 17 methods to increase central dopaminergic neuronal activity and/or decrease central norepinephrine neuronal activity will reduce metabolic disorders and key elements of metabolic disorders. Again, the effect is not specific to a compound(s) but rather to the neuronal physiology that is produced by the compound(s) as described herein. The common denominator among these above methods is their effect to increase the central dopamine to norepinephrine neuronal activity ratio and thereby reduce metabolic disorders and key elements of metabolic disorders. Particularly key aspects of this invention including of the above 17 methods to increase the central dopamine to norepinephrine neuronal activity ratio are that such methods do not appreciably reduce synaptic dopamine levels and do not appreciably raise synaptic norepinephrine levels with long term treatment. In these above 17 method examples, dopamine D1 and/or D2 receptor agonists are utilized at dosages that produce no or not better than modest (less than 50% of maximal response) effects on metabolic disorders and key elements thereof so as to minimize or avoid desensitization, compensation, and/or counteraction. Furthermore, such dopamine/norepinephrine neuronal activity ratio-increasing therapeutics may induce reduction of metabolic disorders by mechanisms that do not induce hypophagia however that may correct hyperphagia (i.e., to euphagia) if it exists but this effect is not required in all cases for the manifestation of reduction of metabolic disorders and key elements thereof. Moreover, in the cases of combined therapy with compound(s) that increase central dopaminergic neuronal activity plus compound(s) that decrease central noradrenergic neuronal activity, an unpredicted synergism or magnitude of effect occurs respecting the magnitude of the reduction in metabolic disorders and key elements thereof. Additionally, in the cases of combined therapy with compound(s) that increase central dopaminergic neuronal activity plus compound(s) that decrease central noradrenergic neuronal activity, the combined therapy effects to reduce metabolic disorders or key elements of metabolic disorders are uniquely multifactorial compared to either individual therapy alone (i.e, increasing dopaminergic neuronal activity or decreasing norepinephrine neuronal activity), in the ability to produce maximal beneficial effects across several metabolic disorders or key elements thereof simultaneously, such as upon multiple disorders from among hyperglycemia, body weight, body fat, hyperinsulinemia, insulin resistance, a pro-coagulative state, a pro-inflammatory state, dyslipidemia, vascular disease, endothelial dysfunction, renal disease, and/or hepatic steatosis. The effects of a dopamine/norepinephrine neuronal activity ratio-increasing therapeutic to maximally reduce metabolic disorders or key elements of metabolic disorders are time of day dependent and are most effective if administered at about the time of the onset of daily locomotor activity (preferably within a time period of about from 4 hours before to about 4 hours after the onset of locomotor activity).

In another aspect, the present invention is directed to a method for treating the metabolic syndrome, Type 2 diabetes obesity, or prediabetes, including key elements of these metabolic disorders comprising the step of: administering to a patient suffering from the metabolic syndrome, Type 2 diabetes, obesity, or prediabetes including key elements of these metabolic disorders a pharmaceutical composition comprising at least one compound that simultaneously stimulates (1) an increase in central dopaminergic neuronal activity level, and (2) a decrease in central noradrenergic neuronal activity level.

As described above, the literature on dopamine and norepinephrine involvement in the regulation of metabolism is quite confounding with a poor characterization of what critical neurophysiological events are required respecting dopaminergic and noradrenergic neurons to elicit a maximally beneficial and sustained effect on metabolic disorders while minimizing potential adverse influences of such neurophysiological events. Prior work has focused on modulation of specific neurotransmitter receptor sites (i.e., utilizing receptor agonists or antagonists) but has not defined the neuronal physiology that is being sought after or that is crucial in eliciting a maximal beneficial effect to reduce metabolic disorders. The present invention now has delineated methods of simultaneously increasing central dopaminergic neuronal activity and decreasing central noradrenergic neuronal activity that produce maximally beneficial and sustained effects on metabolic disorders while minimizing potential adverse influences of such methods to elicit these metabolic effects. In other words, the present invention has both ascertained 1) what neurophysiological events are required to produce maximally beneficial and sustained effects on metabolic disorders while minimizing potential adverse influences of such methods to elicit these metabolic effects and 2) how best to induce these neurophysiological events that produce maximally beneficial and sustained effects on metabolic disorders while minimizing potential adverse influences of such methods to elicit these metabolic effects. As such the present invention is able to facilitate improvements in metabolic disorders without untoward adverse effects unattainable with other previous methods of utilizing dopamine or norepinephrine affecting modulators. The differences and advantages of this therapeutic approach over other different methods that are dopamine affecting approaches such as those in U.S. Pat. Nos. 6,855,707, 6,004,972; 5,866,584; 5,756,513; and 5,468,755 and dopamine receptor agonist stimulation or dopamine/norepinephrine reuptake inhibitors or release stimulators, but that are not this invention, include:

1. Increased Potency: Synergistic or augmenting effects of methods used to increase central dopaminergic neuronal activity plus methods used to decrease central noradrenergic activity are much more potent than the maximum tolerated and effective dose of dopamine receptor agonist therapy or dopamine/norepinephrine reuptake inhibitor or release stimulator therapy to reduce metabolic disorders, particularly to reduce multiple metabolic disorders simultaneously. Consequently, the effects of these methods of this invention to reduce metabolic disorders are not practically attainable with dopamine receptor agonist therapy. Several examples of this much improved comparative efficacy are given in the Examples section below.

2. Decreased Adverse-effect Profile: Synergistic or additive effects of the present invention allow for a decrease in the dose of agents used to increase dopaminergic or decrease noradrenergic neuronal activity to produce the desired metabolic effect. The decreased dose(s) of such agents reduces the potential for and occurrence of adverse, side-effects. Since high doses of agents that increase dopaminergic neuronal activity, particularly dopamine receptor agonists, are associated with untoward side-effects that can make long-term therapy impractical for many subjects (Cincotta A H et al, Exp Opin Invest Drugs, 1999, 10:1683), such method allows for the benefits of such dopamine agonist therapy to manifest at previously ineffective or less effective low doses thus avoiding the untoward side-effects of the high doses. High doses of agents such as dopamine/norepinephrine reuptake inhibitors that might increase dopaminergic neuronal activity and that may as a lone treatment be needed to produce any metabolic effect are well known to produce undesirable adverse effects that preclude their practical and effective use to treat metabolic disorders and these adverse effects can be avoided while maintaining or yet improving the metabolic effect by lowering the dose of these agents and coupling such therapy with an agent that decreases noradrenergic neuronal activity. Examples of this method would be use of post-synaptic dopamine receptor agonists or dopamine and norepinephrine reuptake inhibitors with compounds that decrease noradrenergic neuronal activity with or without agents that increase endogenous synaptic dopamine level.

3. Decreased Counteraction: The current invention circumvents the problem induced by decreased endogenous dopamine release that is the result of dopamine D2 receptor agonist binding to pre-synaptic dopamine autoreceptors that thereby blocks its effectiveness in treating metabolic disease.

Decreased Desensitization: An important advantage of the present invention is avoidance of desensitization as defined herein. Prior neuromodulatory treatments, particularly the use of dopamine D2 receptor agonists or D1 receptor agonists, result in the neuronal activity becoming "desensitized" to the application of drugs, and ultimately lead to ineffectiveness of these treatments. By contrast, the present invention minimizes desensitization of stimulation of dopaminergic neurons while potentiating this effect with methods for the inhibition of noradrenergic neurons, and thus makes the treatments highly effective. Desensitization is reduced by the complete avoidance of or the reduced dosage use (to doses that produce no or modest [less than 50% of maximal metabolic benefit by themselves]) of dopamine D2 receptor or D1 receptor agonists. This invention reduces the potential for desensitization of metabolic effects observed with dopamine D2 receptor agonists such as bromocriptine or dopamine D1 receptor agonists by either completely eliminating their use to increase dopaminergic neuronal activity or reducing their dose to levels that minimize or practically eliminate desensitization and that are ineffective by themselves. Preferably, the net effect of the intervention is to remain as increased dopamine to noradrenaline neuronal activity longterm, without loss of potency, and this is another critical component to the present invention.

4. Increased benefit to risk or adverse effect ratio for the therapy

In one embodiment, the method of the present invention includes administering to a subject in need of treatment for a metabolic disorder, including the metabolic syndrome, Type 2 diabetes, obesity, and/or prediabetes, including key elements of metabolic disorders, a pharmaceutical composition comprising (1) at least one compound that stimulates an increase in central dopaminergic neuronal activity level in said subject, and (2) at least one compound that stimulates a decrease in central noradrenergic neuronal activity level in said subject. In an alternative embodiment, the pharmaceutical composition may include a single compound that stimulates an increase in central dopaminergic neuronal activity level as well as stimulates a decrease in central noradrenergic neuronal activity level. It is also contemplated that two, three, four, or more such compounds, each capable of simultaneously stimulating an increase in central dopaminergic neuronal activity level as well as stimulates a decrease in central noradrenergic neuronal activity level, may be used in the pharmaceutical composition. In all embodiments, however, the ratio of dopaminergic neuronal to noradrenergic neuronal activity within the hypothalamus is increased.

The increase in central dopaminergic neuronal activity level can take place by any mechanism. In preferred embodiments, the increase in central dopaminergic neuronal activity level occurs by including in the pharmaceutical composition at least one compound that stimulates an increase in central dopaminergic neuronal activity level. Preferably, such compounds include, but are not limited to, specific dopamine reuptake inhibitors, dopamine/norepinephrine reuptake inhibitors used in conjunction with compounds that reduce norepinephrine neuronal activity, dopamine presynaptic transporter inhibitors, dopamine presynaptic autoreceptor antagonists; presynaptic dopamine release enhancers, post synaptic dopamine receptor agonists used in conjunction with or without compounds that circumvent agonist-induced decrease in synaptic dopamine level, dopamine synthesis stimulators, and/or dopamine catabolism inhibitors. Examples of useful compounds that stimulate an increase in central dopaminergic neuronal activity level include, but are not limited to, GBR-12935 (known as 1-[2-(diphenylmethoxy)ethyl]-4-(3-phenylpropyl)piperazine); BDNF (Brain Derived Neurotrophic Factor), quinpirole ((4aR-trans)-4,4-a,5,6,7,8,8a,9-octahydro-5-propyl- 1H-pyrazolo[3,4-g]quinoline); quinelorane, SKF38393 (1-phenyl-7,8-dihydroxy-2,3,4,5-tetrahydro-1H-3-benzazepine hydrochloride); deprenyl (also known as "Selegiline"); apomorphine, pramipexole (sold commercially under the name "Mirapex"), GBR-12909 ("Vanoxerine", 1-2-(bis (4-fluorophenyl)-methoxy)-ethyl-4-(3-phenylpropyl)piperazine); talexipole, dihydroergotoxine (hydergine), bromocriptine, lisuride, terguride, methylphenidate, bupropion, nomefensine, phenylaminotetralins, and combinations thereof.

The inhibition of noradrenergic neuronal activities may also be accomplished via any mechanism. In preferred embodiments, stimulation of a decrease in central noradrenergic activity level occurs by administration of at least one compound that results in a decrease in central noradrenergic activity level. Preferably, such compounds include, but are not limited to, postsynaptic noradrenergic receptor blockade compounds (antagonists), inhibitors of noradrenalin release, inhibitors of noradrenalin synthesis, activators of noradrenalin presynaptic reuptake, and activators of noradrenalin catabolism presynaptically and in the synapse. Examples of useful compounds that decrease central noradrenergic activity level include, but are not limited to, prazosin (1-(4-amino-6,7-dimethoxy-2-quinazolinyl)-4-(2-furanylcarbonyl)piperizine): propranolol (1-(isopropylamino)-3-(1-naphthyloxy)-2-propanol); clonidine (2-(2,6-dichloroanilino)-2-imidazoline); fusaric acid (5-butyl-2-pyridinecarboxylic acid; 5-butylpicolinic acid); dopamine; phenoxybenzamine; phentolamine, (3-[[(4,5-dihydro-1H-imidazol-2-yl)methyl](4-methylphenyl)amino]phenol; 2-[N-(m-hydroxyphenyl-p-toluidineomethyl)imidazoline); guanfacine (sold under the brand name "Tenex"); pantethine, and combinations thereof.

As indicated above, the method of the invention may also include administration of a pharmaceutical composition that includes a single or individual compound that simultaneously stimulates an increase in central dopaminergic neuronal activity level and a decrease in central noradrenergic neuronal activity level. Examples of such compounds include catecholamine modifiers, such as dopamine, and histamine receptor 1 agonists, such as 8R-lisuride and phenylaminotetralins. Combinations of these compounds may also be employed.

Since the Metabolic Syndrome is diagnosed as having several criteria (as described above), and further encompasses vascular abnormalities such as endothelial dysfunction, vascular pro-inflammatory condition, and vascular pro-coagulative conditions, the treatment of Metabolic Syndrome according to the present invention further includes a. Treatment of endothelial dysfunction or pro-oxidant state associated with cardiovascular disease;
b. Treatment of hypertension, vascular pro-inflammatory state, pro-coagulative state, and pro-oxidant state simultaneously. Examples of pro-inflammatory state blood markers include but are not limited to: C-reactive protein, serum amyloid A protein, interleukin-6, interleukin-1, Tumor Necrosis Factor-alpha, homocysteine, and white blood cell count. Examples of pro-coagulative state blood markers include but are not limited to: hematocrit viscosity, red cell aggregation, plasminogen activator inhibitor-1, fibrinogen, van Willebrand factor, Factor VII, Factor VIII, and Factor IX;
c. Treatment of at least two of hypertension, vascular pro-inflammatory state, pro-coagulative state, or pro-oxidant state simultaneously; and
d. Treatment of at least one of hypertension, vascular pro-inflammatory state, or pro-coagulative state.

The endothelium can modify circulating factors as well as synthesize and release factors that influence cardiovascular health and disease. Endothelium dysfunction is characterized by alterations in endothelium modulation of the vasculature that favor or potentiate vasoconstriction, a pro-coagulant state, and/or a pro-inflammatory state as well as other biochemical process that all contribute to the initiation and progression of atherosclerosis (Am. J. Cardiol. 91(12A): 3H-11H, 2003; Am. J, Cardiol. 115 Suppl 8A:99S-106S, 2003).

The compounds of the invention are preferably administered internally, e.g., orally, subcutaneously, transdermally, sublingually, or intravenously, in the form of conventional pharmaceutical compositions, for example in conventional enteral or parenteral pharmaceutically acceptable excipients containing organic and/or inorganic inert carriers, such as water, gelatin, lactose, starch, magnesium stearate, talc, plant oils, gums, alcohol, Vaseline, or the like. The pharmaceutical compositions can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical compositions may also contain other therapeutically active materials. The pharmaceutical compositions of the invention can be made using conventional methods know in the art of pharmaceutical manufacturing.

The pharmaceutical compositions of the invention should include an amount of the compound(s) of the invention effective for treatment of the metabolic syndrome obesity, prediabetes, or Type 2 diabetes. The effective dosage will depend on the severity of the diseases and the activity of the particular compound(s) employed, and is thus within the ordinary skill of the art to determine for any particular host mammal or other host organism. Suitable dosages may be, for example, in the range of about 0.001 to about 100 mg per kg for a human being, and more preferably from about 0.01 to about 50 mg per kg for a human being.

The ratio of the compound(s) that stimulates an increase in central dopaminergic neuronal activity level to the compound(s) that stimulates a decrease in central noradrenergic neuronal activity level in the pharmaceutical composition generally ranges from about 500:1 to 1:500 on a weight-to-weight basis (w:w), and more preferably from about 100:1 to 1:100 on a weight-to-weight basis (w:w).

Multiple circadian central neural oscillations govern the regulation and coordination of multiple physiological (e.g., metabolic) events in the periphery as a function of their circadian phase relationship, described in U.S. Pat. No. 5,468,755 and herein incorporated in entirety by reference. One such circadian rhythm governing metabolic status is the central (hypothalamic) circadian rhythm of dopaminergic activity. It has previously been observed that phase shifts in the circadian rhythm of central dopaminergic activities influenced the status of obesity or diabetes. However, it has now been surprisingly found that phase shifts away from the healthy normal circadian rhythm of central or hypothalamic dopaminergic activity by environment, diet, stress, genetics and/or other factors are somehow also operative in a much different and broader physiological regulatory system and potentiate and lead to the multiple complex metabolic pathologies of and associated with metabolic syndrome as described herein. Furthermore, it has now been found that resetting these aberrant central dopaminergic circadian rhythms back towards that of the healthy normal state results in simultaneous improvements in the multiple complex pathologies of and associated with metabolic syndrome as described herein. As described above, metabolic syndrome and its associated pathologies represent a different pathology from diabetes or obesity, the cause of which is unknown. However, subjects with metabolic syndrome have much greater risk of developing cardiovascular disease than subjects without the syndrome. Inasmuch as obesity and type 2 diabetes are not always associated with metabolic syndrome and vice versa, it is clear that this major health risk represents a separate and unique metabolic state with unique characteristics. Adjusting the circadian rhythm of central dopaminergic activities by various means may be employed to reduce the many pathologies of and associated with this syndrome, for example aberrant vascular tone, vascular health, endothelial function, glucose and lipid metabolism, immune system functions specifically influencing the vasculature, insulin action, and blood coaguability. This same circadian dopaminergic resetting methodology may also be utilized to treat cardiometabolic risk, a cluster of physiological pathologies of common or discordant origin that converge to increase risk of cardiovascular disease. These risk factors include those of metabolic syndrome, but also inflammation, endothelial dysfunction, hypercholesterolemia, diabetes, obesity, smoking, gender, and age. Rather than just increasing dopaminergic activity with central dopamine agonists to improve metabolic syndrome, cardiometabolic risk and their associated pathologies, one may better influence these conditions by timing the administration of such dopamine agonists to coincide with the daily peak in central dopaminergic activities of healthy subjects of the same species to derive maximal benefit from such dopamine agonist therapy in treating these conditions.

In further accordance with this invention, the use of dopamine agonists to treat the Metabolic Syndrome (obesity, insulin resistance, hyperlipidemia, and hypertension), non-metabolic pathologies associated with MS (a pro-inflammatory state, a pro-coagulative state, pro-oxidant state, and/or endothelial dysfunction), arteriosclerosis, and/or cardiovascular disease, all in subjects with or without Type 2 diabetes, is applied during specific daily intervals to maximize the effectiveness of such treatment. Use of such centrally acting dopamine agonists for treatment of the metabolic and non-metabolic vascular disorders described herein may be potentiated by their administration at the appropriate time(s) of day. Circadian rhythms of dopaminergic activity within the central nervous system, and particularly the phase relations of these dopaminergic neuronal rhythms with other circadian neuronal activities such as serotonergic neuronal activities have been demonstrated to regulate peripheral glucose and lipid metabolism in a manner dependent upon the phase of the daily peak in circadian central dopaminergic activity. Consequently, increases in dopaminergic activity at particular times of day versus others produce maximal effectiveness in improving metabolic diseases and disorders such as type 2 diabetes, obesity, pre-diabetes, metabolic syndrome, cardiometabolic risk, hypertension, dyslipidemia, insulin resistance, hyperinsulinemia, hepatic steatosis, renal disease, cardiovascular disease, cerebrovascular disease, and peripheral vascular disease and biomarkers of impending vascular disease. As such, maximized successful treatment of these aforementioned pathologies and abnormalities may be accomplished by appropriately timed daily administration of centrally acting dopamine agonist(s). Because such dopamine agonist therapy attacks a root cause of these metabolic disorders (central dysregulation of global peripheral metabolism) it is possible to effectuate improvements in several metabolic pathologies in a simultaneous fashion that is not generally achievable by other conventional means that attack particular specific symptoms of metabolic disease for example hypertension or high cholesterol or hyperglycemia by acting at specific downstream peripheral targets such as biochemical pathways within liver or muscle. Such a treatment effect is currently lacking in the general armamentarium of therapeutics for metabolic diseases. Moreover, central dopamine agonist therapy may be coupled to peripheral acting therapeutic agents such as anti-diabetes agents, antihypertensive agents, cholesterol lowering agents, anti-inflammatory agents, or anti-obesity agents to produce additive improvements in metabolic disease such as obesity or type2 diabetes or particular aspects of metabolic disease such as hypertension associated with obesity or type 2 diabetes.

The present invention is further described in detail by means of the following Examples. All parts and percentages are by weight unless explicitly stated otherwise.

EXAMPLES

Generally

Four different groups of animals exhibiting the metabolic syndrome, obesity, prediabetes or Type 2 diabetes are studied. Within each disease group, animals are randomly assigned to one of four different treatment groups and treated with either saline as control, central dopamine neuronal activity activator(s), central noradrenergic neuronal activity inhibitor(s), or a molecular entity or entities that is/are both a central dopaminergic neuronal activity activator and central noradrenergic neuronal activity inhibitor, respectively.

Within each disease model of study and relative to the control group the dopaminergic neuronal activator/noradrenergic neuronal activity inhibitor group exhibits the greatest improvement in metabolism (decrease in obesity, dyslipidemia, hypertension, insulin resistance, vascular function, impaired fasting glucose, impaired glucose tolerance, and/or hyperglycemia) that is also significantly better than that of either the dopaminergic activator or noradrenergic inhibitor groups which may each be better than (i.e., demonstrate improvement in metabolic disease relative to) controls. An unexpected synergism between the dopaminergic neuronal activity stimulator(s) and noradrenergic neuronal activity inhibitors(s) is observed relative to the effects on improvement of obesity, the metabolic syndrome with associated conditions, prediabetes, and/or type 2 diabetes.

Additionally, in studies of the use of selective dopamine reuptake inhibitors compared to dopamine/norepinephrine reuptake inhibitors on metabolic disorders demonstrate that the selective dopamine reuptake inhibitor is more effective in treating metabolic disorders than are the dopamine/norepinephrine reuptake inhibitors. Also, dopamine/norepinephrine reuptake inhibitors plus compounds that reduce norepinephrine neuronal activity (and therefore block the norepinephrine effect of the dopamine/norepinephrine reuptake).

Example 1

Introduction

GBR 12909 (1-(2-[bis(4-Fluorophenyl)methoxy]ethyl)-4-(3-phenylpropyl)piperazine dihydrochloride) is a specific dopamine reuptake inhibitor. Systemic administration of GBR 12909 can increase the dopaminergic to noradrenergic neuronal activity in the central nervous system. A study was conducted to determine the effects of GBR 12909 upon blood glucose and plasma free fatty acid levels in obese, diabetic mice (ob/ob strain). The ob/ob mouse is hyperphagic, obese, insulin resistant, diabetic and dyslipidemic due to the absence of functional leptin as a result of a mutation in this gene. Starvation or calorie restriction of these mice leads to increases in plasma free fatty acid levels that can function over the long term to worsen diabetes. This animal model also exhibits renal, hepatic steatosis, cerebrovascular and cardiovascular disease as a result of its metabolic derangements.

Methods and Results

Different groups of obese, diabetic female (ob/ob) mice (body weight of approximately 33 g) maintained on 12 hour daily photoperiods, housed one per cage and allowed to feed ad libitum were randomized to once daily treatment with either a specific dopamine reuptake inhibitor, GBR 12909 at a dose of 30 mg/kg body weight (n=5-7) or vehicle (control group; n=5-7) for a 14 day period. On the fifteenth day of the study and approximately 24 hours after the final treatment animals were sacrificed and blood samples were obtained for the analyses of blood glucose and plasma free fatty acid and triglyceride levels. Relative to controls, GBR 12909 treatment reduced blood glucose from 455+/−50 mg/dl to 145+/−25 mg/dl. Relative to controls, GBR 12909 treatment reduced plasma free fatty acid levels from 780+/−40 uM to 450+/−20 uM. Relative to controls, GBR 12909 treatment reduced final body weight from 42+/−2 g to 28+/−0.5 g and plasma triglyceride level by approximately 32%.

Discussion

The present studies demonstrate that treatment of obese, diabetic animals with a specific dopamine reuptake inhibitor, GBR 12909, that increases the dopamine to noradrenaline neuronal activity ratio by selectively increasing synaptic dopamine levels results in improvements in type 2 diabetes, obesity, and metabolic syndrome.

Example 2

Introduction

GBR 12909 is a specific dopamine reuptake inhibitor. Its use can increase the dopaminergic to noradrenergic neuronal activity in the central nervous system. However, by combining GBR 12909 with clonidine, a noradrenergic alpha 2 receptor agonist with preferential affinity for presynaptic alpha 2 sites, it is possible to further increase the dopamine to noradrenaline neuronal activity ratio in the central nervous system. A study was conducted to determine the interactive effects of GBR 12909 and clonidine on blood glucose level in ob/ob mice.

Methods and Results

Obese, diabetic female ob/ob mice (body weight of approximately 28 g) with mild diabetes were maintained on 14 hour daily photoperiods, housed one per cage and allowed to feed ad libitum. Different groups of these animals were randomized to once daily treatment with either a specific dopamine reuptake inhibitor, GBR 12909 at an approximate dose of 20 mg/kg body weight (n=4), or clonidine at an approximate dose of 0.1 mg/kg (n=5), these same dosages of GBR 12909 plus clonidine (n=3), or vehicle (control group; n=5-7) for a 14 day period. On the fifteenth day of the study and approximately 24 hours after the final treatment animals were sacrificed and blood samples were obtained for the analyses of blood glucose levels. Relative to controls, GBR 12909 treatment had no effect on blood glucose (202+/−41 to 221+/−31 mg/dl) as did not clonidine (202+/−41 versus 250+/−35 mg/dl), however GBR 12909 plus clonidine reduced the blood glucose level from 202+/−41 to 121+/−15 mg/dl.

Discussion

These studies indicate that increasing the dopaminergic to noradrenergic neuronal activity ratio, in this case by inhibiting presynaptic dopamine reuptake of synaptic dopamine plus reducing noradrenaline release by stimulation of presynaptic alpha 2 receptors results in a synergistic effect to improve hyperglycemia and type 2 diabetes. This positive interactive effect allows for potential lower effective dosages of the compounds to be administered that in turn may also reduce dose dependent side effects of these compounds to the subject.

Example 3

Introduction

Amphetamine is a selective presynaptic dopamine release enhancer. It also acts as a presynaptic noradrenergic release enhancer but at higher dosages that will counter the effect of the dopamine reuptake inhibition activity to improve metabolism. However, addition of a dopamine D2 receptor agonist will act to reduce any amphetamine-induced increase in synaptic noradrenaline level and therefore should produce a more pronounced desired effect on metabolic disease than amphetamine or the D2 receptor agonist alone. A study was conducted to determine the effects of low dose amphetamine (3 mg/kg) with or without the dopamine D2 receptor agonist bromocriptine (5-<10 mg/kg dose) upon body weight gain, blood glucose, plasma free fatty acid and triglyceride levels in obese, diabetic mice (ob/ob strain). It has been previously demonstrated in the literature that bromocriptine treatment at this dose has no effect on feeding, body weight, or blood glucose in these animals (Life Sciences 61:951, 1997). The ob/ob mouse is hyperphagic, obese, insulin resistant, diabetic and dyslipidemic due to the absence of functional leptin as a result of a mutation in this gene. Starvation or calorie restriction of these mice leads to increases in plasma free fatty acid levels that can function over the long term to worsen diabetes.

Methods and Results

Obese, diabetic female ob/ob mice (body weight of approximately 33 g) maintained on 12 hour daily photoperiods, housed one per cage and allowed to feed ad libitum were randomized to once daily treatment with either a selective dopamine reuptake inhibitor, amphetamine at a dose of 3 mg/kg body weight (n=5-7), or amphetamine (3 mg/kg) plus bromocriptine (5-<10 mg/kg; n=5-7) or vehicle (control group; n=5-7) for a 14 day period. On the fifteenth day of the study and approximately 24 hours after the final treatment animals were sacrificed and blood samples were obtained for the analyses of blood glucose, plasma free fatty acid and triglyceride levels. Relative to control ob/ob mice, bromocriptine treatment at the dose employed in this study has been shown not to reduce blood glucose or body weight. Relative to controls, amphetamine reduced blood glucose levels from 422+/−46 mg/dl to 348+/−22 mg/dl however, amphetamine plus bromocriptine treatment reduced blood glucose from 422+/−46 mg/dl to 250+/−20 mg/dl. Relative to controls, amphetamine treatment reduced plasma triglyceride levels from 175+/−21 mg/dl to 70+/−7 mg/dl, however amphetamine plus bromocriptine treatment reduced plasma triglyceride levels further to 60+/−4 mg/dl. Relative to controls, amphetamine treatment reduced plasma free fatty acid levels from 900+/−100 uM to 510+/−30 uM, however amphetamine plus bromocriptine treatment reduced plasma triglyceride levels further to 495+/−25 mg/dl. Amphetamine had no effect on final body weight however, amphetamine plus bromocriptine reduced final body weight from 44+/−1 g to 39+/−1.5 g.

Discussion

These findings indicate that increasing the dopamine to noradrenaline neuronal activity ratio by selectively increasing synaptic dopamine levels, in this case by inhibiting its reuptake into presynaptic neurons following its release with a mixed dopamine/noradrenaline reuptake inhibitor at a dose that preferentially effects dopamine reuptake in combination with a dopamine D2 receptor agonist that can reduce amphetamine impact to increase synaptic noradrenaline, can improve type 2 diabetes, dyslipidemia, and indices of metabolic syndrome. Moreover, the interactive effects of these two compounds are synergistic upon improving diabetes, obesity and metabolic syndrome. This positive interactive effect allows for lower effective dosages of the compounds that may also reduce any side effects of these compounds to the subject. These results further demonstrate the synergistic interaction of mixed dopamine/noradrenaline reuptake inhibition and dopamine D2 agonist activity to increase the dopamine to noradrenaline neuronal activity ratio and thereby improve metabolic disease.

Example 4

Introduction

Fusaric acid is a dopamine beta hydroxylase inhibitor that reduces noradrenaline synthesis in noradrenergic neurons. It is not present in dopaminergic neurons and thus exerts no such effect there. SKF38393 is a post-synaptic dopamine D1 receptor agonist with no marked influence on noradrenergic neurons. A study was conducted to determine the interactive effects of fusaric acid plus SKF 38393 on body fat store levels, and blood glucose and plasma triglyceride levels in ob/ob mice. The ob/ob mouse is hyperphagic, obese, insulin resistant, diabetic and dyslipidemic due to the absence of functional leptin as a result of a mutation in this gene.

Methods and Results

Obese, diabetic female ob/ob mice (body weight of approximately 33 g) maintained on 14 hour daily photoperiods, housed one per cage and allowed to feed ad libitum were randomized to once daily treatment with either fusaric acid (15 mg/kg; n=6-8), SKF 38393 (10 mg/kg; n=6-8), both fusaric acid (15 mg/kg) and SKF 38393 (10 mg/kg) (n=6-8), or vehicle (control group; n=6-8) for a 14 day period. On the fifteenth day of the study and approximately 24 hours after the final treatment animals were sacrificed and blood samples were obtained for the analyses of blood glucose, plasma free fatty acid and triglyceride levels. Relative to controls, fusaric acid raised blood glucose from 380+/−30 mg/dl to 430+/−30 mg/dl and SKF 38393 reduced blood glucose to 290+/−55 mg/dl. However, fusaric acid plus SKF 38393 reduced blood glucose to 180+/−20 mg/dl. Fusaric acid treatment raised plasma triglyceride level from 155+/−15 mg/dl to 170+/−27 mg/dl, while SKF 38393 lowered plasma triglyceride level to 130+/−7 mg/dl and fusaric acid plus SKF 38393 treatment lowered plasma triglyceride level to 115+/−4 mg/dl. Neither fusaric acid nor SKF 38393 had any effect on retroperitoneal fat pad weight (735+/−43 mg and 735+/−50 mg, respectively versus control value of 727+/−25 mg) however, the combination of fusaric acid plus SKF 38393 reduced retroperitoneal fat pad weight to 680+/−25 mg.

Discussion

These findings indicate that increasing the dopamine to noradrenaline neuronal activity ratio by stimulating post-synaptic dopamine D1 receptors plus inhibiting the synthesis of noradrenaline at the dopamine beta hydroxylase step, can improve type 2 diabetes, obesity and metabolic syndrome. Moreover, the interactive effects of these two compounds are synergistic upon improving diabetes, obesity and metabolic syndrome. This positive interactive effect allows for lower effective dosages of the compounds that may also reduce any dose dependent side effects of these compounds to the subject.

Example 5

Figure 2:
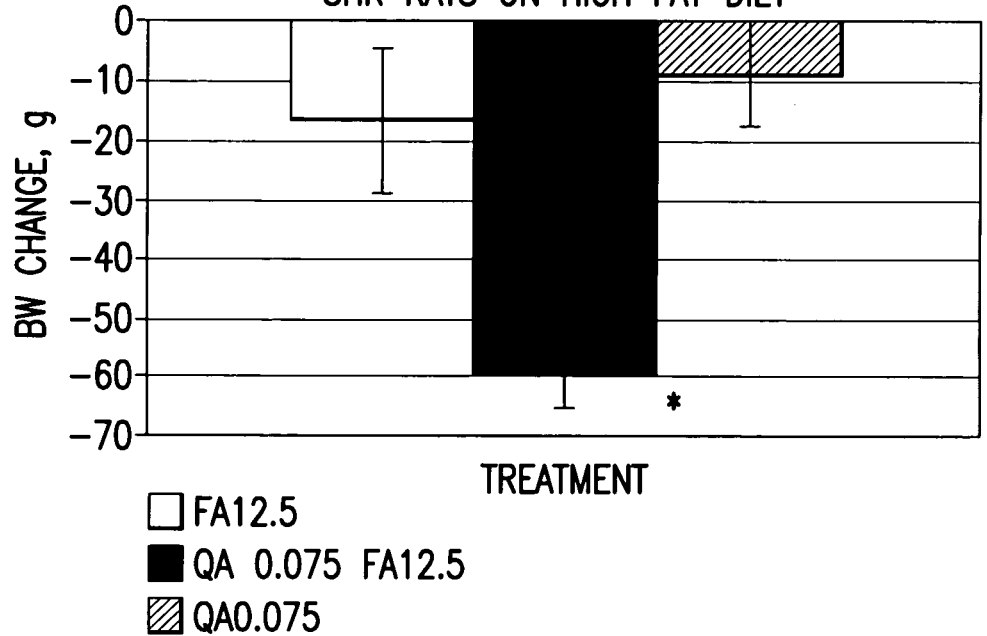
FIG. 2 is a graph showing the effect of quinelorane plus fusaric acid on body weight change in rats.
Figure 3:
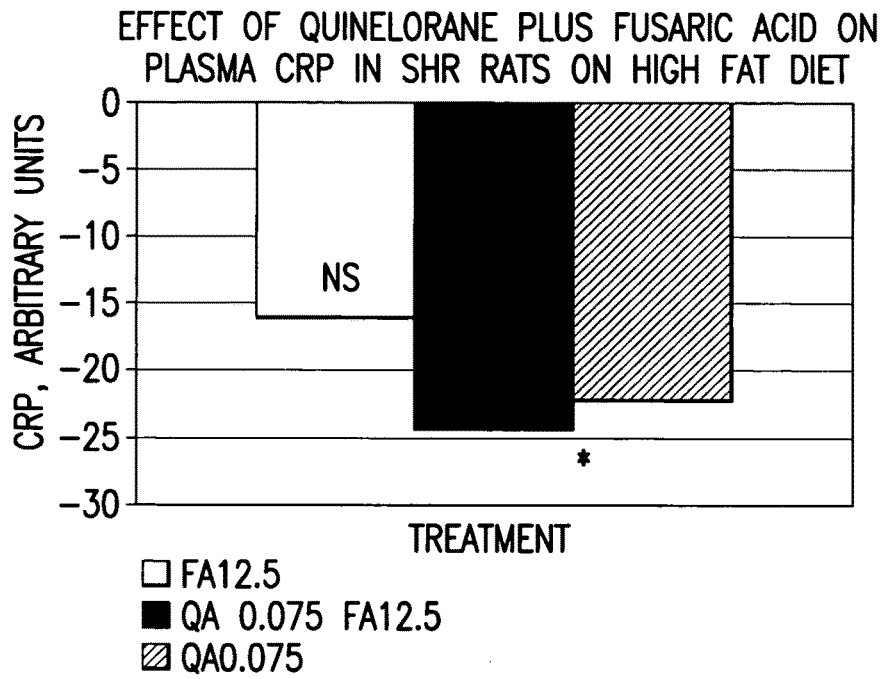
FIG. 3 is a graph showing the effect of quinelorane plus fusaric acid on plasma CRP in SHR rats on a high fat diet.
Figure 4:
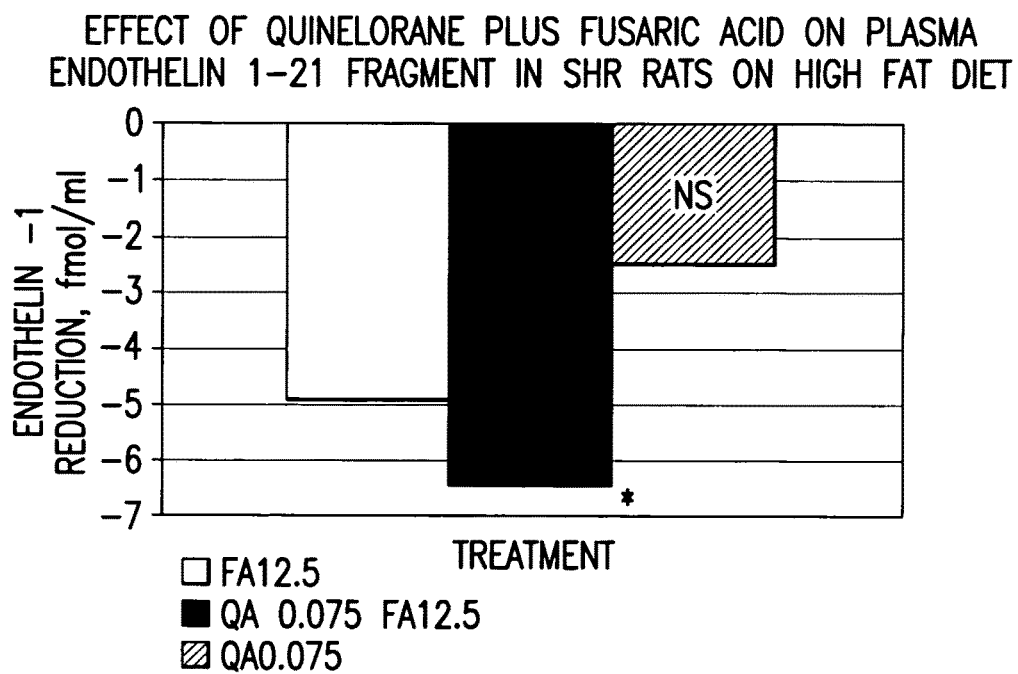
FIG. 4 is a graph showing the effect of quinelorane plus fusaric acid on plasma endothelin 1-21 fragment in SHR rats on a high fat diet.
Figure 5:
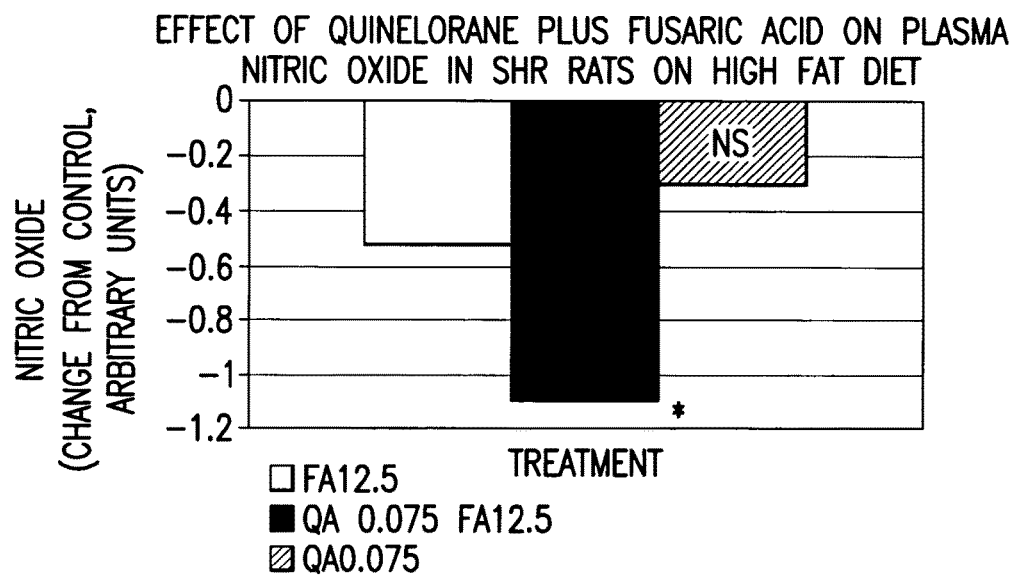
FIG. 5 is a graph showing the effect of quinelorane plus fusaric acid on plasma nitric oxide in SHR rats on a high fat diet.
Figure 6:
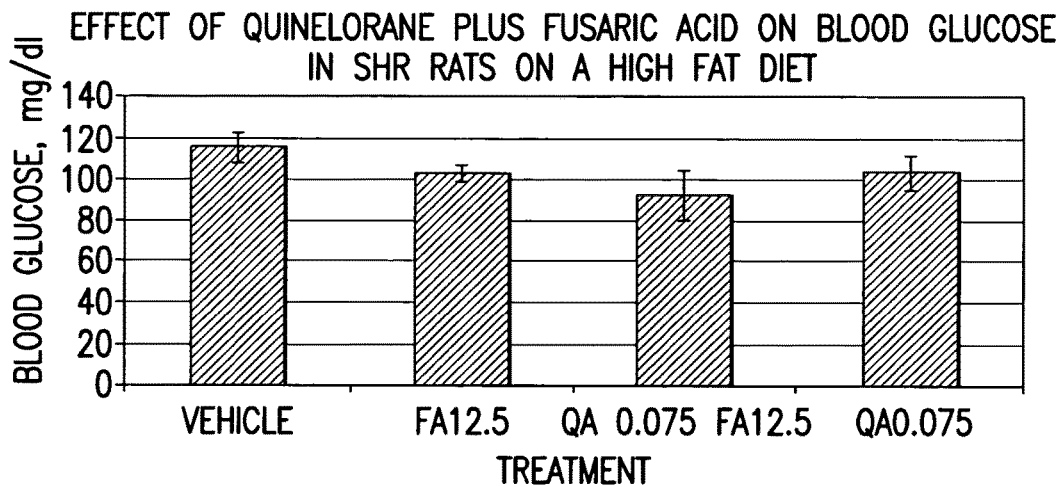
FIG. 6 is a graph showing the effect of quinelorane plus fusaric acid on blood glucose in SHR rats on a high fat diet.

This Example demonstrates the effect of post-synaptic dopamine agonist plus dopamine beta hydroxylase inhibitor on metabolic disorders in high fat fed, hypertensive SHR rats. Male SHR rats were maintained on 14 hour daily photoperiods and fed a high fat diet (60% of energy from fat; 5.24 kcal/gram weight) for 3 weeks and then divided into different groups and treated with either quinelorane (Q; a dopamine D2/D3 mixed receptor agonist) (0.075 mg/kg), fusaric acid (FA; a dopamine beta hydroxylase inhibitor) (12.5 mg/kg), quinelorane (0.075 mg/kg) plus FA (Q/FA) (12.5 mg/kg), or vehicle at 13 hours after light onset for 17 days. The doses of Q and FA were set at less than half maximal to effect central dopamine receptor binding functions and dopamine beta hydroxylase activity, respectively. Such treatment with the high fat diet resulted in significant body weight gain relative to standard chow fed animals. Blood pressure measurements were taken at 14 days of treatment and animals were sacrificed at 18 days of treatment for analyses of body fat and humoral factors and metabolites. Relative to the Q or FA groups, the Q/FA group produced robust and synergistic reductions in change from baseline body weight (x vs y) while the vehicle control group did not reduce weight gain at all. Importantly, the Q group exhibited desensitization to the effects on weight loss early in the treatment regimen so that this group on average regained weight loss to baseline values by treatment end. The modest if any effects of weight loss in the Q and FA groups were amplified several-fold in the combination group indicating a clear synergism on weight loss (FIGS. 1 and 2). Also, such Q/FA treatment relative to vehicle reduced plasma endothelin-1 (FIG. 3), nitric oxide (FIG. 4), and C-reactive protein levels (FIG. 5) and inasmuch as Q had no significant effect on nitric oxide or endothelin 1-21 fragment plasma levels and FA had no significant effect on CRP, such Q/FA reductions on nitric oxide, endothelin-1 and CRP were more than additive of the individual compounds for these parameters (0+X>X). Respecting blood glucose, although both Q and FA reduced glucose level relative to vehicle, only the Q/FA regimen normalized blood glucose in these animals relative to vehicle (FIG. 6). The Q/FA group was the only group that produced significant reductions in all parameters tested.

Example 6

Figure 7:
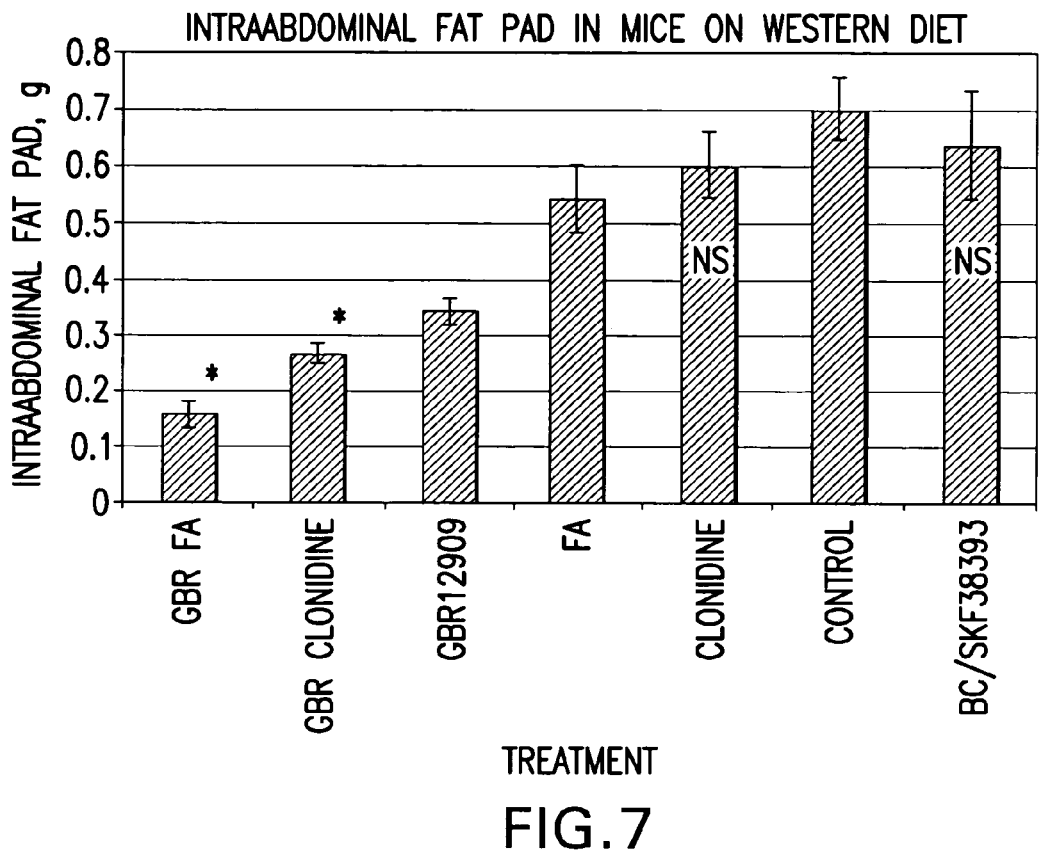
FIG. 7 is a graph showing intraabdominal fat pad in mice on a western diet.

Female C57 Black mice were maintained on a 12 hour daily photoperiod and fed a high simple sugar/moderate fat diet (western diet) for several weeks to induce obesity and then different groups of animals (n=5-8/group) were treated with either GBR 12909 (25 mg/kg), FA (10 mg/kg), clonidine (0.075 mg/kg), GBR (25 mg/kg) plus FA (10 mg/kg), GBR (25 mg/kg) plus clonidine (0.075 mg/kg), bromocriptine (10 mg/kg) plus SKF38393 (10 mg/kg), or vehicle and sacrificed after 14 days of treatment to analyze body fat store levels. Relative to vehicle and the BC/SKF groups, the greatest reduction in body fat store level was observed in the GBR plus FA and GBR plus clonidine groups. Moreover, within these two combination groups the magnitude of the effects were more than additive relative to the effects of each respective compound individually when combined. Clonidine had no effect on body fat store level by itself. The results demonstrate that a selective dopamine reuptake inhibitor plus and presynaptic norpeinephrine alpha 2A agonist or a selective dopamine reuptake inhibitor plus a dopamine beta hydroxylase inhibitor can in each case synergize to reduce body fat in animals fed a high simple sugar/moderate fat diet. FIG. 7 shows the effect of GRB, FA, GBR+FA, clonidine, clomidine+GBR, and BC/SKF on body fat in mice fed a western diet. As shown in FIG. 7, an asterisk denotes a significant difference from control and NS=not significant relative to control.

Example 7

Figure 8:
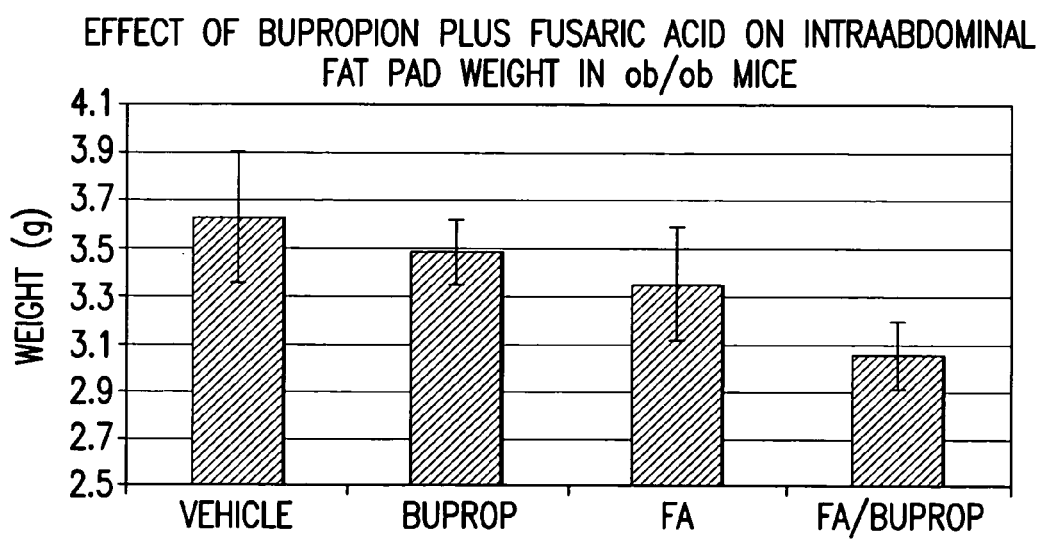
FIG. 8 is a graph showing the effect of bupropion plus fusaric acid on intraabdominal fat pad weight in ob/ob mice.
Figure 9:
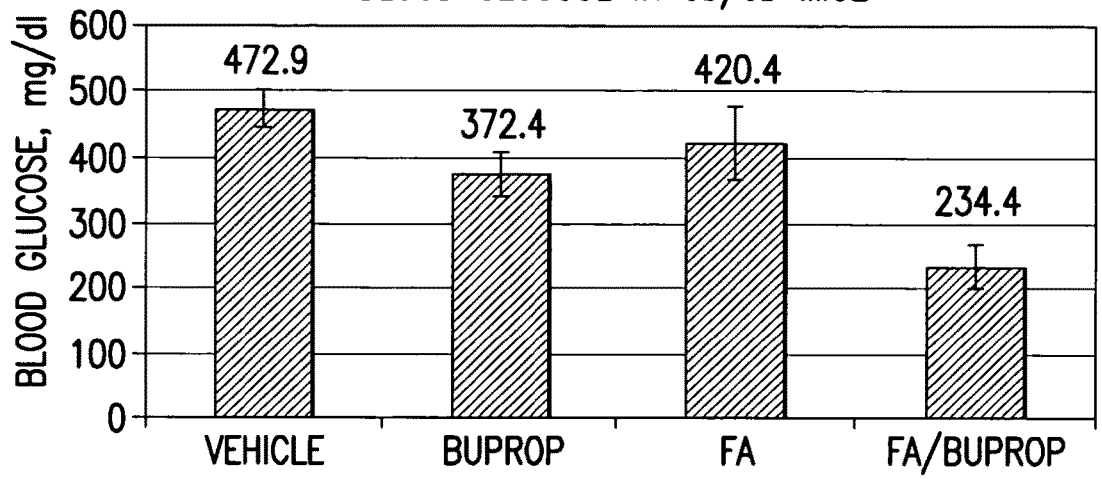
FIG. 9 is a graph showing the effect of bupropion plus fusaric acid on blood glucose in ob/ob mice.

Female obese diabetic mice (ob/ob strain) at 6 weeks of age were fed standard rodent chow and different groups of animals (n=5-7/group) were treated with bupropion (40 mg/kg), FA (10 mg/kg), bupropion (40 mg/kg) plus FA (10 mg/kg), or vehicle for 14 days and then sacrificed for the analyses of blood glucose and body fat store level. Relative to control group, the bupropion plus FA group exhibited the greatest reduction in both blood glucose (hyperglycemia or diabetes) and body fat store level. Moreover, these reductions were more than additive in magnitude relative to the effects of the individual compounds combined. Only the FA/Buproprion (Buprop) group exhibited a significant reduction in body fat relative to the vehicle control group (FIG. 8). The FA/Bupropion group exhibited the greatest reduction in blood glucose and this effect was more than additive compared to the FA and Bupropion groups combined. FA treatment produced no significant effect on blood glucose (FIG. 9).

Example 8

Figure 10:
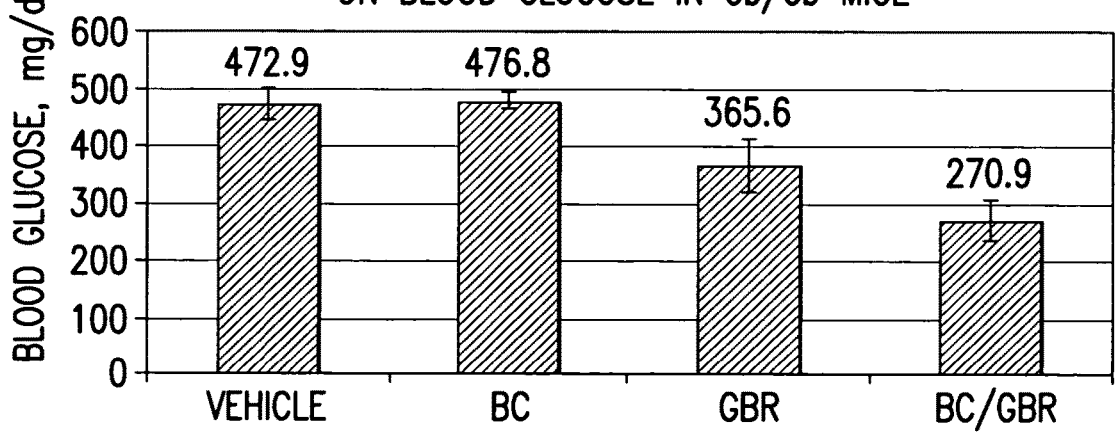
FIG. 10 is a graph showing the effect of bromocriptine plus GBR on blood glucose in ob/ob mice.

The effects of adding GBR (a selective dopamine reuptake inhibitor) to bromocriptine (a dopamine D2 receptor agonist that can reduce central norepinephrine neuronal activity) in an effort to circumvent the impact of the D2 receptor agonist effect to reduce endogenous dopamine and to therefore improve metabolic disorders was examined in ob/ob mice treated with either vehicle, bromocriptine (BC) (10 mg/kg), GBR 12909 (20 mg/kg) or bromocriptine (10 mg/kg) plus GBR 12909 (20 mg/kg). Female ob/ob obese diabetic mice were fed standard chow and different groups of animals (n=5-7 group) were treated daily for 14 days with bromocriptine (to reduce norepinephrine neuronal activity) (10 mg/kg), GBR 12909 (to increase dopaminergic neuronal activity) (20 mg/kg) or with bromocriptine (10 mg/kg) plus GBR 12909 (20 mg/kg), or vehicle. Relative to vehicle controls, the BC plus GBR group exhibited the greatest reduction in blood glucose level (i.e., hyperglycemia or diabetes) and the effect in this group was more than additive compared to the BC and GBR groups alone. The BC/GBR group exhibited the greatest reduction in blood glucose level. BC had no effect on blood glucose level. The BC/GBR effect on blood glucose level was more than additive of the individual effects of BC and GBR combined (FIG. 10)

Example 9

Figure 11:
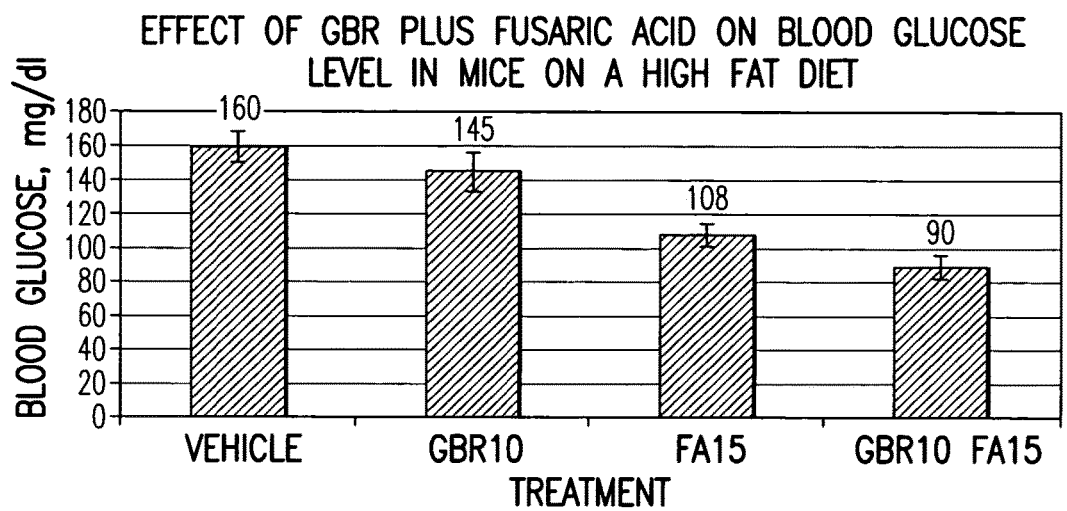
FIG. 11 is a graph showing the effect of GBR plus fusaric acid on blood glucose level in mice on a high fat diet.
Figure 12:
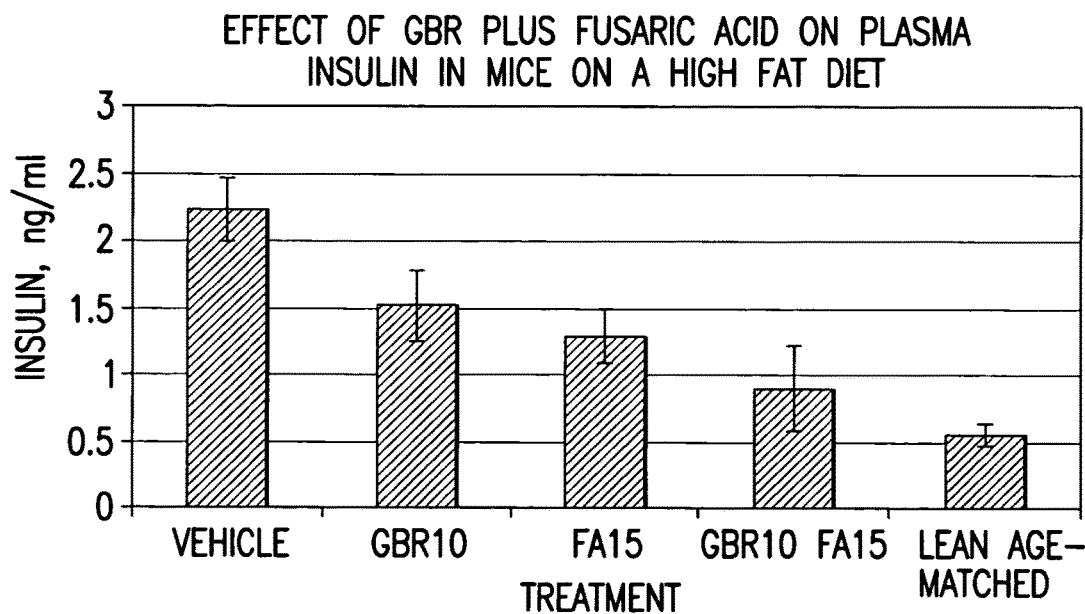
FIG. 12 is a graph showing the effect of GBR plus fusaric acid on plasma insulin in mice on a high fat diet.
Figure 13:
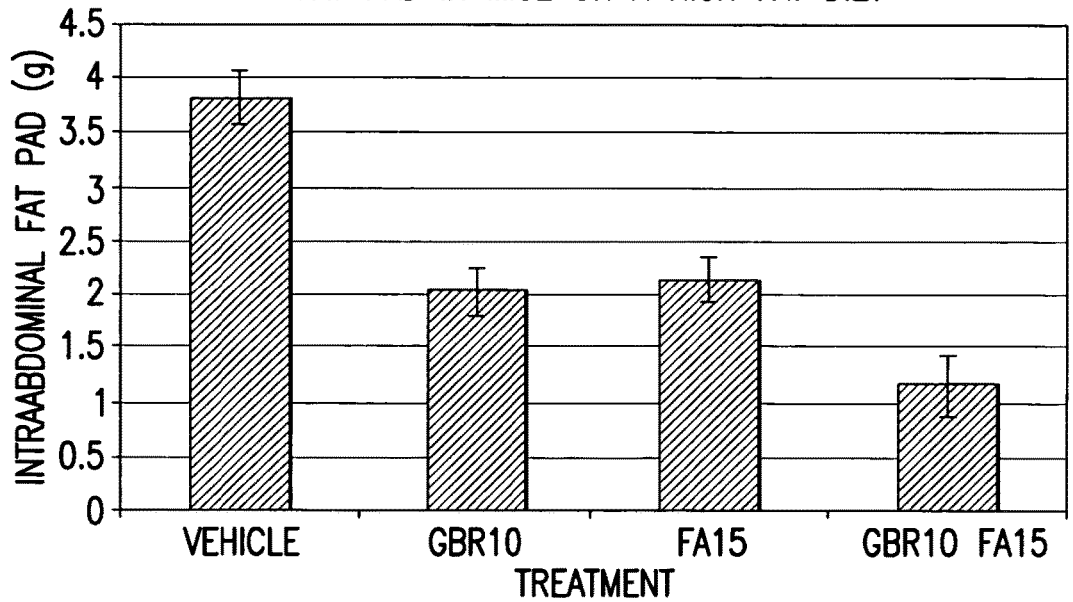
FIG. 13 is a graph showing the effect of GBR plus fusaric acid on intraabdominal fat pad in mice on a high fat diet.
Figure 14:
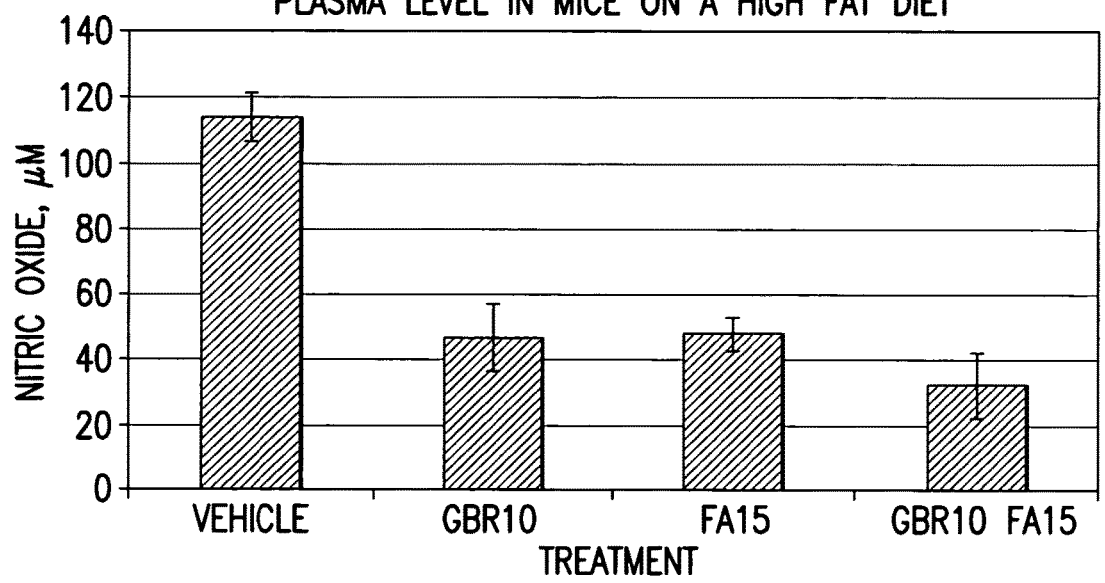
FIG. 14 is a graph showing the effect of GBR plus fusaric acid on nitric oxide plasma level in mice on a high fat diet.
Figure 15:
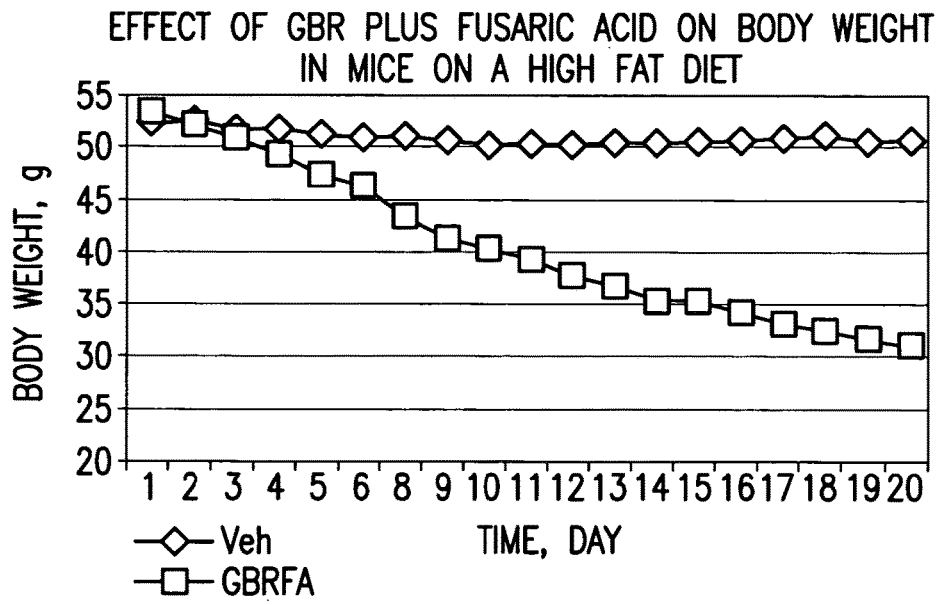
FIG. 15 is a graph showing the effect of GBR plus fusaric acid on body weight in mice on a high fat diet.

Female mice at 4 weeks of age were fed a high fat diet for 20 weeks to induce diabetes and insulin resistance and continued on such diet while treated for 14 days with either GBR 12909 (10 mg/kg), FA (15 mg/kg), GBR 12909 (10 mg/kg) plus FA (15 mg/kg), or vehicle and sacrificed after 14 days of treatment for the analyses of body fat, blood glucose, plasma insulin, and plasma nitric oxide levels. The composite of body fat store level, blood glucose and plasma insulin was reduced the greatest in the GBR/FA group and by a magnitude more than additive of the individual GBR and FA groups combined. Only the GBR/FA group normalized plasma insulin levels. This GBR/FA group also exhibited the greatest reduction in nitric oxide compared to vehicle controls. The greatest effect on blood glucose was exhibited by the GBR/FA group. GBR alone had no significant effect on blood glucose level, so the effect of BGR plus FA on blood glucose was more than additive compared to the individual effects of GBR and FA combined (FIG. 11). Only the GBR/FA group normalized plasma insulin levels to levels not significantly different from lean, insulin sensitive, non-diabetic mice. Both the GBR and FA alone groups had significantly higher plasma insulin levels after treatment when compared to lean controls (FIG. 12). The greatest effect on body fat store reduction was exhibited by the GBR/FA group that was significantly better than either the GBR or FA groups (FIG. 13). The greatest reduction in nitric oxide was exhibited by the GBR/FA group (FIG. 14). GBR/FA treatment of obese mice, fed a high fat diet for 20 weeks and maintained on a high fat diet for 2 additional weeks during treatment resulted in a near normalization of body weight (normal weight for age matched controls=28 grams). This effect was not observed with either GBR or FA treatments alone. Also, there was no desensitization to this dopamine enhancing treatment on this body weight reduction effect as is observed with dopamine D2 receptor agonists (FIG. 15).

Example 10

Figure 16:
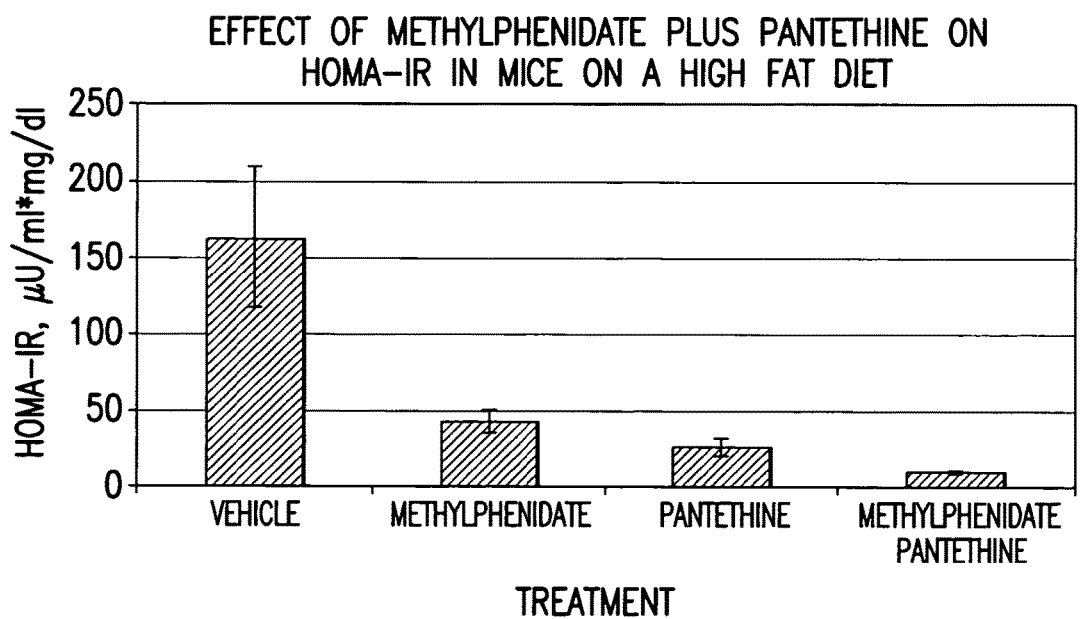
FIG. 16 is a graph showing the effect of methylphenidate plus pantethine on HOMA-IR in mice on a high fat diet.

Male C57Black mice weighing approximately 40 grams were fed a high fat diet from 5 weeks of age for 20 weeks to induce obesity and insulin resistance and then treated with either methylphenidate (a dopamine and norepinephrine reuptake inhibitor) (5 mg/kg), pantethine (a dopamine beta hydroxylase inhibitor) (3 mm), methylphenidate plus pantethine at the respective doses, or vehicle for 12 days and then sacrificed for the analyses of body fat and insulin sensitivity (via HOMA-IR analysis; HOMA-IR values are inversely correlated with insulin sensitivity). Relative to vehicle control group, the methylphenidate plus pantethine group exhibited the greatest improvement in insulin sensitivity and this effect was significantly more than the effect of the individual compounds. The effect of pantethine to counter the norepinephrine-enhancing effect of methylphenidate (via inhibition of norepinephrine synthesis) resulted in an augmentation of the methylphenidate effect (FIG. 16).

Example 11

Figure 17:
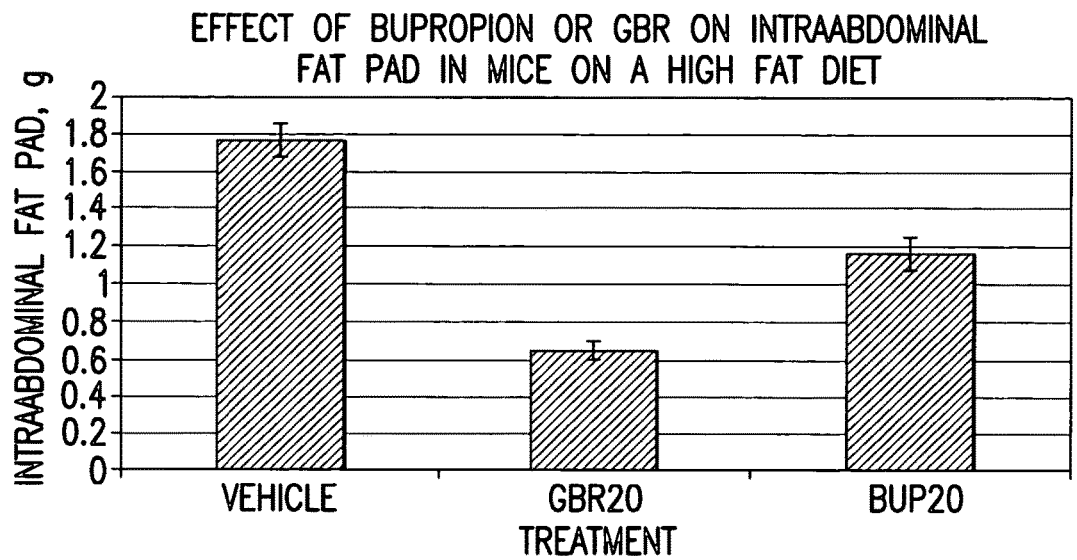
FIG. 17 is a graph showing the effect of bupropion or GBR on intraabdominal fat pad in mice on a high fat diet.
Figure 18:
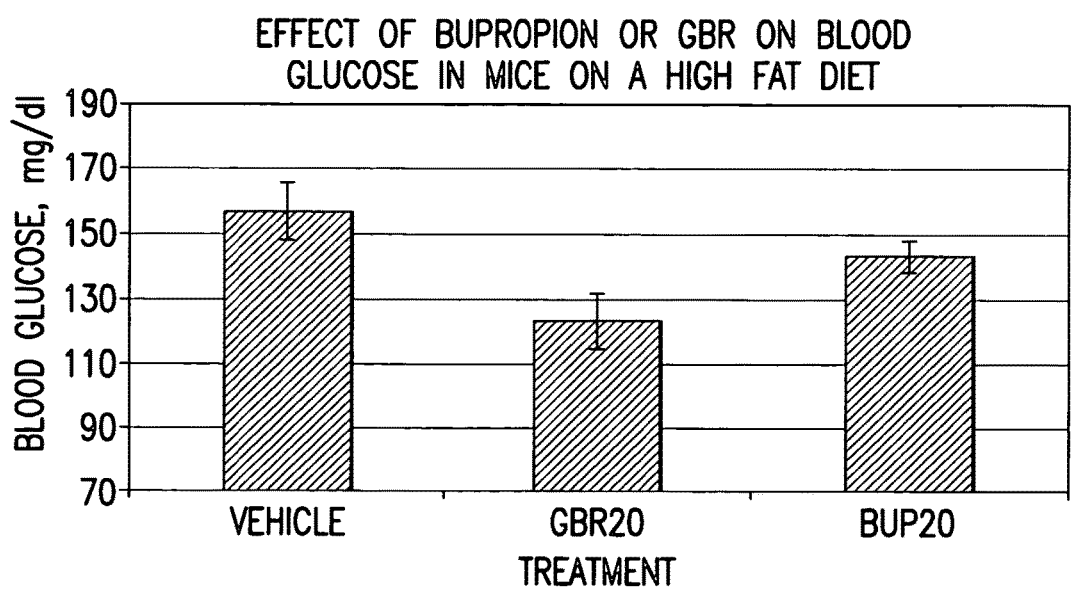
FIG. 18 is a graph showing the effect of bupropion or GBR on blood glucose in mice on a high fat diet.
Figure 19:
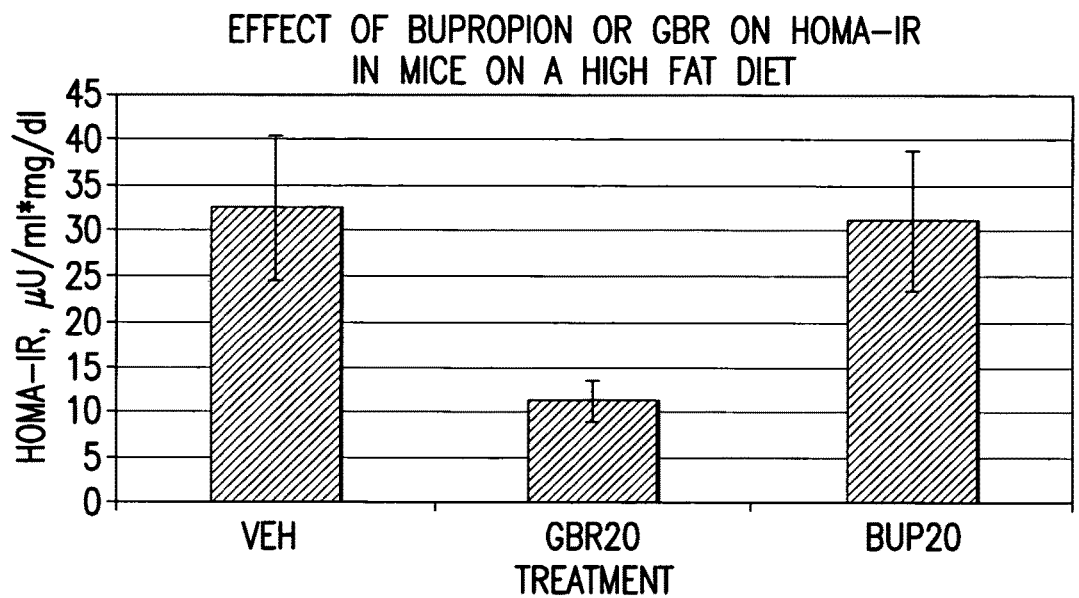
FIG. 19 is a graph showing the effect of bupropion or GBR on HOMA-IR in mice on a high fat diet.

The effect of increasing central dopamine neuronal activity versus increasing central dopamine plus norepinephrine neuronal activity on body fat, blood glucose, plasma insulin, and insulin sensitivity was studied in male mice fed a high fat diet from 4 weeks of age until 24 weeks of age. These mice were maintained on this high fat diet while treated with either GBR (20 mg/kg) (a selective dopamine reuptake inhibitor) or bupropion (20 mg/kg) (a dopamine and norepinephrine reuptake inhibitor) at doses that approximate their 50% maximal effective dose for these functions in vivo in rodents. Equal dose administration of these compounds to high fat fed mice demonstrated that GBR was much more effective at reducing body fat, blood glucose, plasma insulin, and insulin resistance than bupropion. These results indicate that increasing the central dopamine neuronal activity (via a selective dopamine reuptake inhibitor) is more effective than increasing central dopamine and norepinephrine neuronal activity (via a dopamine and norepinephrine reuptake inhibitor) in reducing metabolic disorders and that if one removes the norepinephrine neuronal activity enhancing effects of these dopamine/norepinephrine reuptake inhibitor compounds one can improve their effects on metabolic disorders. GBR significantly reduced body fat compared to vehicle and Bupropion treatment (FIG. 17). GBR treatment significantly reduced blood glucose (hyperglycemia and diabetes) relative to vehicle and Bupropion treatment groups (FIG. 18). GBR treatment significantly reduced HOMA-IR values compared to vehicle and Bupropion treatment groups (FIG. 19).

Example 12

Figure 20:
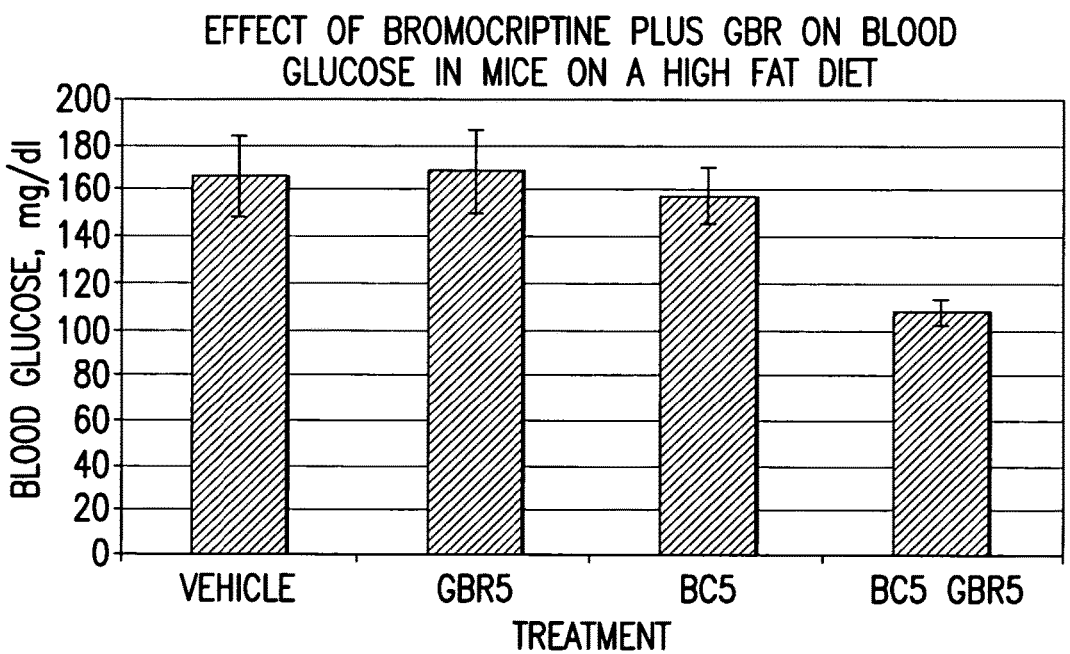
FIG. 20 is a graph showing the effect of bromocriptine plus GBR on blood glucose in mice on a high fat diet.
Figure 21:
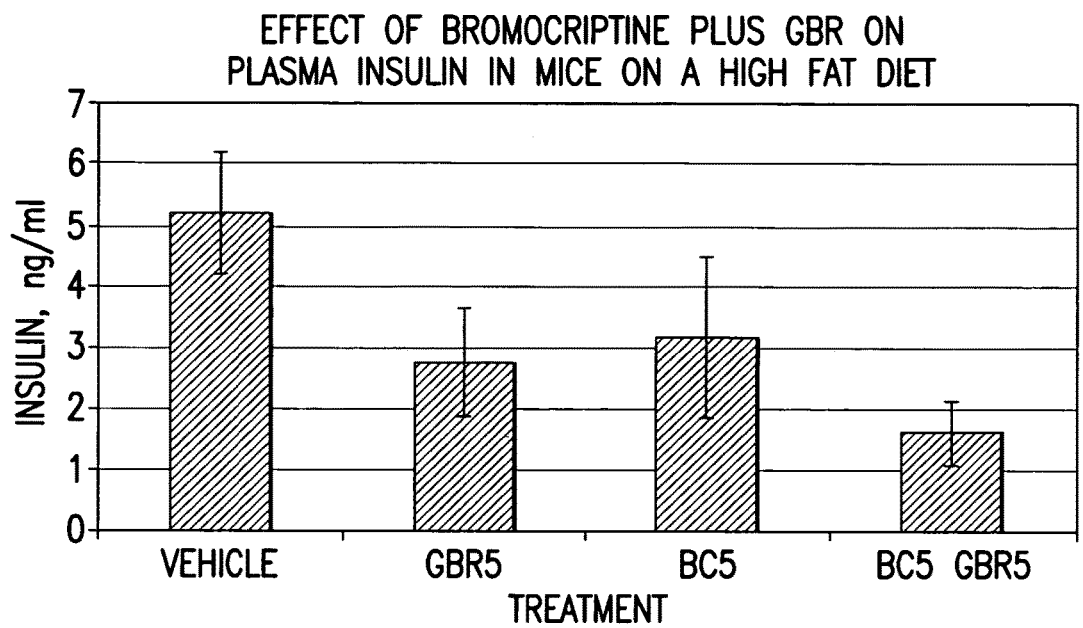
FIG. 21 is a graph showing the effect of bromocriptine plus GBR on plasma insulin in mice on a high fat diet.
Figure 22:
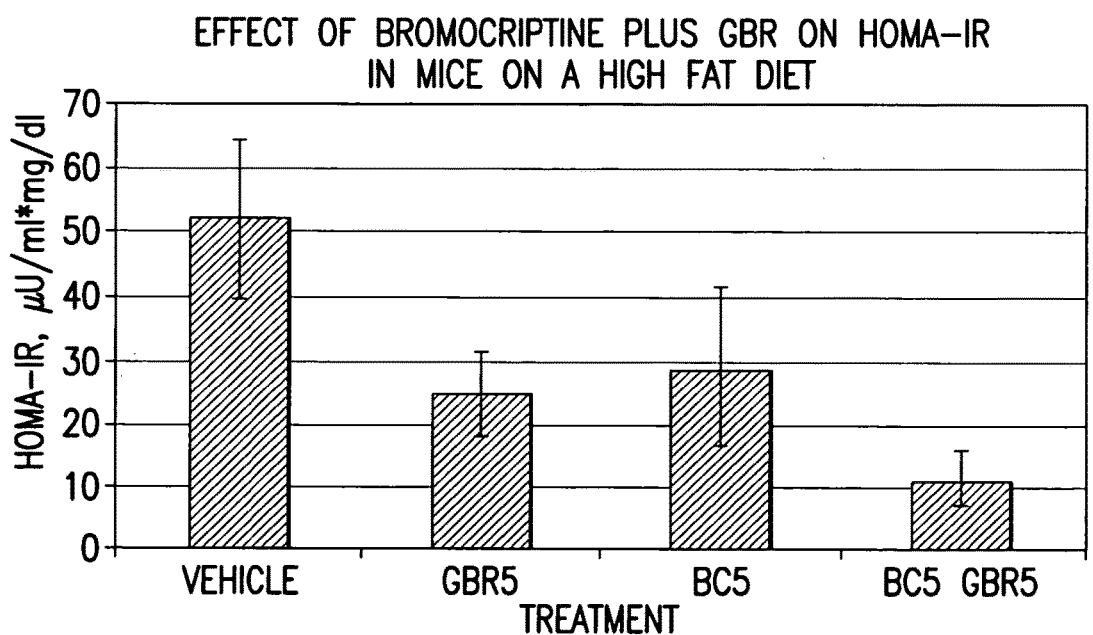
FIG. 22 is a graph showing the effect of bromocriptine plus GBR on HOMA-IR in mice on a high fat diet.

The effects of adding GBR (a selective dopamine reuptake inhibitor) to bromocriptine (a dopamine D2 receptor agonist that can reduce central norepinephrine neuronal activity) in an effort to circumvent the impact of the D2 receptor agonist effect to reduce endogenous dopamine and to therefore improve metabolic disorders was examined in mice fed a high fat diet for 20 weeks and then treated with either vehicle, bromocriptine (BC) (5 mg/kg), GBR 12909 (5 mg/kg) or bromocriptine (5 mg/kg) plus GBR 12909 (5 mg/kg). The BC/GBR group was the only group that exhibited a reduction in blood glucose level (i.e., hyperglycemia and diabetes) indicating a clear synergistic effect of these compounds. The BC/GBR group exhibited the greatest reduction in insulin resistance as well. Since the BC effect on insulin resistance was not significantly different from control, the BC/GBR effect on insulin resistance was more than additive compared to the individual treatments combined. Again, increasing central dopaminergic neuronal activity and decreasing central norepinephrine neuronal activity simultaneously produces synergistic reductions in metabolic disorders. Only the BC/GBR treatment group reduced blood glucose level and the effect was also significantly greater than in the BC or GBR groups as well (FIG. 20). The greatest reduction in plasma insulin was observed in the BC/GBR treatment group. BC alone had no effect on plasma insulin level (FIG. 21). The greatest significant reduction in HOMA-IR was observed in the BC/GBR treatment group. BC alone had no significant effect on HOMA-IR (FIG. 22).

Example 13

Figure 23:
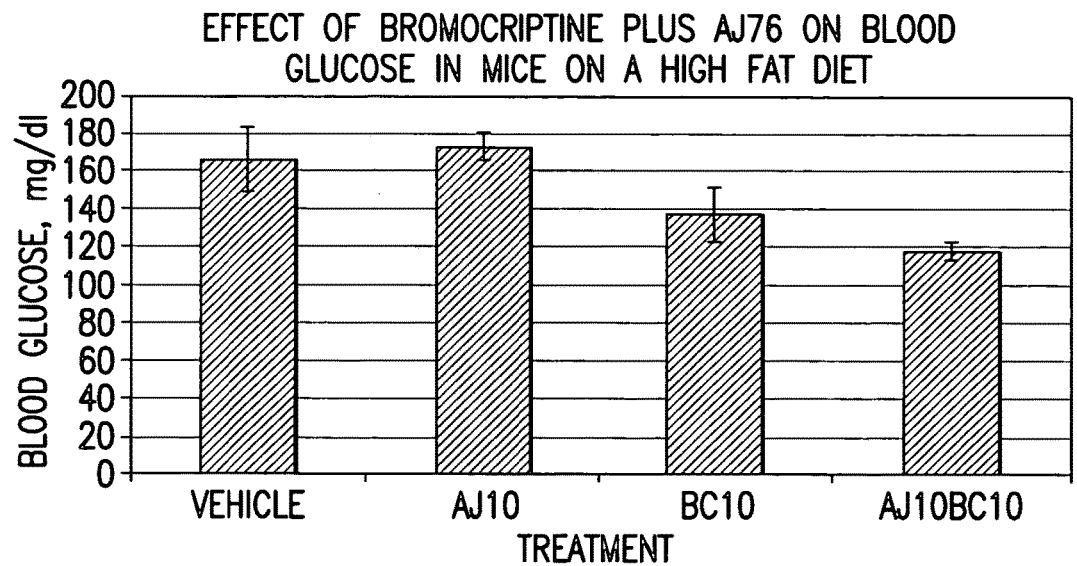
FIG. 23 is a graph showing the effect of bromocriptine plus AJ76 on blood glucose in mice on a high fat diet.

The effects of adding AJ76 (a selective dopamine autoreceptor antagonist) to bromocriptine (a dopamine D2 receptor agonist that can reduce central norepinephrine neuronal activity) in an effort to circumvent the impact of the D2 receptor agonist effect to reduce endogenous dopamine and to therefore improve metabolic disorders was examined in mice fed a high fat diet for 20 weeks and then treated with either vehicle, bromocriptine (BC) (10 mg/kg), AJ76 (10 mg/kg), (BC) (10 mg/kg) plus AJ76 (10 mg/kg), or vehicle. Relative to vehicle controls only the BC/AJ76 group exhibited a significant reduction in plasma glucose level (i.e., hyperglycemia and diabetes) demonstrating a clear synergistic effect of the two compounds on blood glucose control (i.e., diabetes). Only the BC/AJ76 treatment resulted in a significant reduction in blood glucose relative to controls. The reduction in blood glucose in this group was greater than in either the AJ76 or BC group as well (FIG. 23).

Example 14

Figure 24:
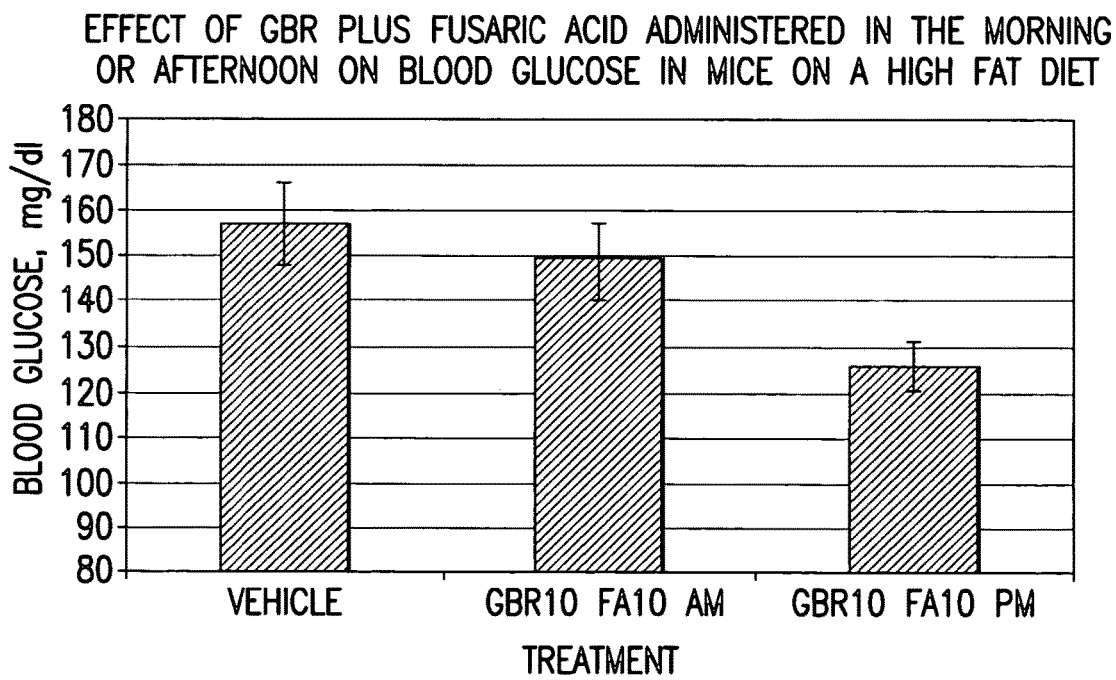
FIG. 24 is a graph showing the effect of GBR plus fusaric acid administered in the morning or afternoon on blood glucose in mice on a high fat diet.

The effects of time of day upon the impact of increasing central dopaminergic neuronal activity and reducing central norepinephrine neuronal activity with non-dopamine D2 receptor agonists was investigated in mice made diabetic by being fed a high fat diet. Mice held on 12 hour daily photoperiods and fed a high fat diet for 20 weeks were divided into different groups and treated with GBR (10 mg/kg) plus FA (10 mg/kg) at light onset (morning) or at light offset, or vehicle for 14 days while maintained on this diet and then analyzed for effects on blood glucose and glycerol levels. Relative to vehicle control and morning treated groups, the afternoon treated group exhibited the greatest reduction in plasma glucose level (i.e., on reducing hyperglycemia and diabetes). Actually, the morning treatment did not produce any significant change in blood glucose level relative to control. These results demonstrate that the effects of increasing central dopaminergic neuronal activity and reducing central norepinephrine neuronal activity with non-dopamine D2 receptor agonists on metabolic disorders is time-of-day dependent. The afternoon treatment also reduced plasma glycerol levels. Only the afternoon (PM) treatment of GBR/FA reduced hyperglycemia in these mice relative to control (FIG. 24).

In total, the above 14 examples demonstrate that a variety of different means and compounds all that share the neurophysiological aspect of increasing central dopaminergic neuronal activity level and decreasing central norepinephrine neuronal activity level result in marked and often synergistic improvements in a wide variety of metabolic disorders. It can be concluded that increasing central dopaminergic neuronal activity level and decreasing central norepinephrine neuronal activity level by any means will result in such reductions in metabolic disorders and key elements thereof. Drugs such as dopamine/norepinephrine reuptake inhibitors can be combined with compounds that block the norepinephrine neuronal activity enhancing aspect of these drugs to further enhance their effects on metabolic disorders. Also, combing compounds that increase central dopaminergic neuronal activity level with those that decrease central norepinephrine neuronal activity level allows for the reduction in the dose levels of these drugs to generate the interactive, augmented effect on metabolism. This in turn, results in reductions of side-effects. In all the above studies, no major central nervous system side-effects were observed as may be the case with higher dosages of these compounds. Therefore, this treatment strategy, that can employ a myriad of different compounds to achieve the object of increasing central dopaminergic neuronal activity level and decreasing central norepinephrine neuronal activity level results in a safe and effective means of treating metabolic disorders.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

What is claimed is:

1. A method for treating a patient suffering from a metabolic disorder,
   comprising the step of:
   administering to a patient suffering from a metabolic disorder selected from the group consisting of metabolic syndrome, Type 2 diabetes, obesity and prediabetes, a pharmaceutical composition comprising:
   (1) one compound that stimulates an increase in central dopaminergic neuronal activity level in said subject, said compound selected from the group consisting of GBR-12935, quinpirole, SKF38393, benzazapine, deprenyl, apomorphine, pramipexole, GBR-12909, methylphenidate, phenylaminotetralins, quinelorane, talexipole, bromocriptine, bupropion, L-dopa, and nomifensine, and combinations thereof, said compound administered at a dosage ranging from 0.075 to 10 mg/kg/day, except if the compound is L-dopa it is administered at a dosage ranging from 1 to 50 mg/kg/day, and
   (2) one compound that stimulates a decrease in central noradrenergic neuronal activity level in said subject, said compound selected from the group consisting of prazosin, propranolol, clonidine, fusaric acid, dopamine, phenoxybenzamine, phentolamine, guanfacine, pantethine, and combinations thereof, said compound administered at a dosage ranging from 0.075 to 10 mg/kg/day, except if the compound is pantethine, it is administered at a dosage ranging from 1 to 50 mg/kg/day;
   wherein the dosage of each of said compound that stimulates an increase in central dopaminergic neuronal activity and said compound that stimulates a decrease in central noradrenergic neuronal activity in combination, provides a therapeutic effect greater than the additive effect of administering the same dosage of each of said compounds alone;
   wherein said pharmaceutical composition is administered to said patient between four hours before and four hours after waking;
   with the proviso that said pharmaceutical composition is not (a) a combination of a dopamine D1 receptor agonist and any of a dopamine D2 receptor agonist, a noradrenergic alpha 1 receptor antagonist, or a noradrenergic alpha 2 receptor agonist; (b) a combination of dopamine D1 receptor agonist and a dopamine D2 receptor agonist in further combination with at least one of a noradrenergic alpha 1 receptor antagonist or a noradrenergic alpha 2 receptor agonist; or (c) a combination of a D2 agonist, and at least one agent, not a D2 agonist, selected from the group consisting of noradrenergic alpha 1 antagonists and noradrenergic alpha 2 agonists.

2. The method of claim 1, wherein said compound that stimulates an increase in central dopaminergic neuronal activity level in said subject is selected from the group consisting of benzazapine, methylphenidate, bromocriptine, bupropion and L-dopa.

3. The method of claim 2, wherein said compound that stimulates a decrease in central noradrenergic neuronal activity level in said subject is selected from the group consisting of dopamine and pantethine.

4. The method of claim 2, wherein said compound that stimulates an increase in central dopaminergic neuronal activity level in said subject is L-dopa.

5. The method of claim 3, wherein said compound that stimulates a decrease in central noradrenergic neuronal activity level in said subject is pantethine.

* * * * *